United States Patent [19]

Stanwell et al.

[11] Patent Number: 5,610,185
[45] Date of Patent: Mar. 11, 1997

[54] METHOD FOR THE TREATMENT OF HYPERPROLIFERATIVE EPITHELIAL SKIN DISEASES BY TOPICAL APPLICATION OF HYDROXYLATED AROMATIC PROTEIN CROSS-LINKING COMPOUNDS

[75] Inventors: Caroline Stanwell; Stuart H. Yuspa; Terrence R. Burke, Jr., all of Bethesda, Md.

[73] Assignee: The United States of America as represented by the Department of Health and Human Services, Washington, D.C.

[21] Appl. No.: 389,845

[22] Filed: Feb. 17, 1995

[51] Int. Cl.⁶ .................... A61K 31/235; A61K 31/47
[52] U.S. Cl. ................... 514/544; 514/309; 514/312
[58] Field of Search ....................... 514/544, 332, 514/309, 312

[56] References Cited

U.S. PATENT DOCUMENTS

| | | | |
|---|---|---|---|
| 4,421,927 | 12/1983 | Picart | 424/248.55 |
| 4,833,240 | 5/1989 | Maignan et al. | 514/62 |
| 4,925,877 | 5/1990 | Umezawa et al. | 514/630 |
| 5,360,815 | 11/1994 | Fortin, et al. | 514/432 |

OTHER PUBLICATIONS

Umezawa, et al., 1990 "Inhibition of epidermal growth factor–induced DNA synthesis by tyrosine kinase inhibitors" *FEBS Lett.* 260(2):198–200.

Umezawa, et al., 1992 "Inhibition of epidermal growth factor receptor functions by tyrosine kinase inhibitors in NIH3T3 cells" *FEBS Letts.* 314(3):289–292.

Hori, et al., 1992 "Inhibition of tyrosine Kinase and *src* oncogene functions by stable erbstatin analogues" *J. Antibiotics*, 45(2):280–282.

Burke, 1994 "Protein–tyrosin kinase: potential targets for anticancer drug development" *Stem Cells* 12:1–6.

Markovits, et al., 1994 "Inhibition of DNA topoisomerases I and II and induction of apoptosis by erbstatin and tyrphostin derivatives" *Biochem. Pharm.* 48(3):549–560.

*Primary Examiner*—Jerome D. Goldberg
*Attorney, Agent, or Firm*—Morgan & Finnegan, L.L.P.

[57] ABSTRACT

The present invention relates to a method of treating hyperproliferative epithelial lesions by topical administration. The method prevents growth and actively cross-links these aberrant cells, thereby killing the cells. The present invention is useful in control and prevention of hyperproliferative epithelial disorders, such as HPV-infected cell lesions, actinic keratosis, melanomas, and malignant and pre-malignant carcinomas.

9 Claims, 15 Drawing Sheets
(2 of 15 Drawing(s) in Color)

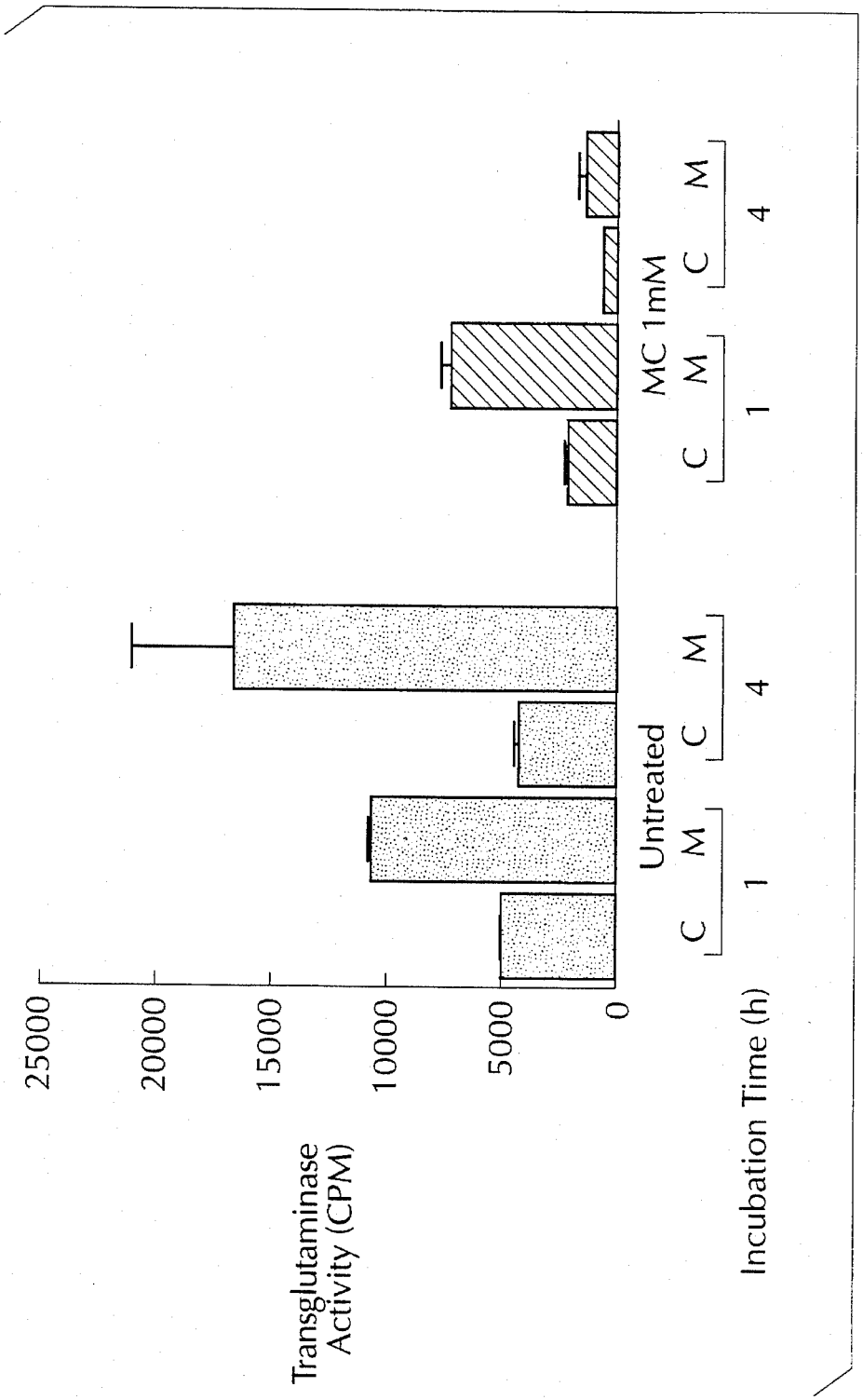

4°C

37°C

FIG. 12
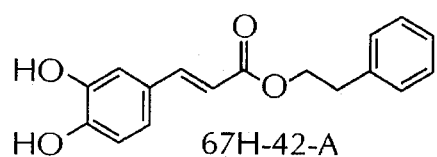
67H-42-A
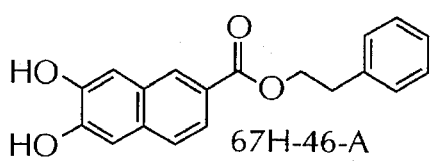
67H-46-A
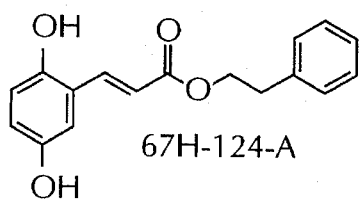
67H-124-A
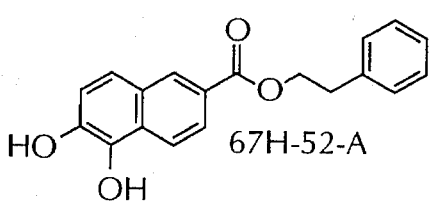
67H-52-A
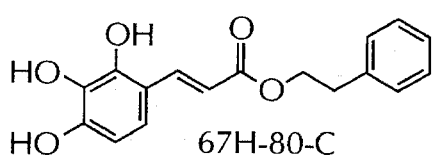
67H-80-C
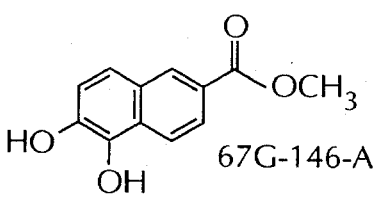
67G-146-A
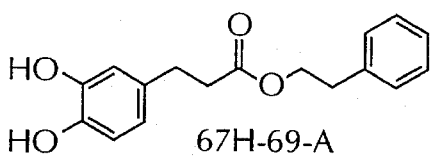
67H-69-A
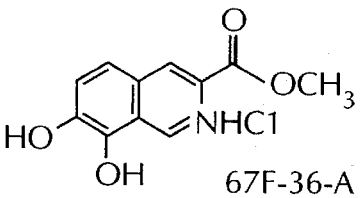
67F-36-A
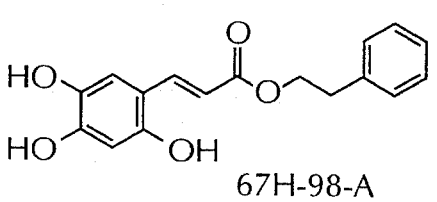
67H-98-A
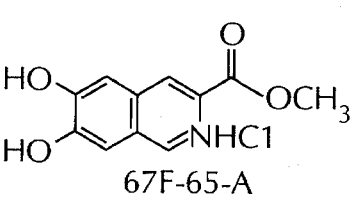
67F-65-A
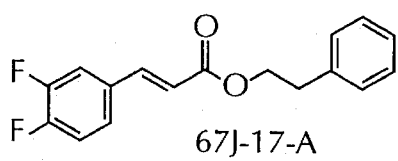
67J-17-A
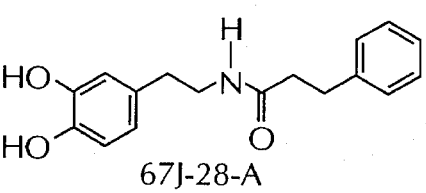
67J-28-A
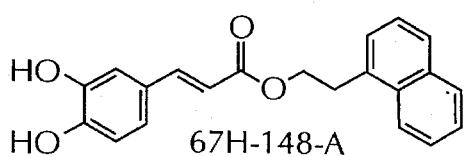
67H-148-A
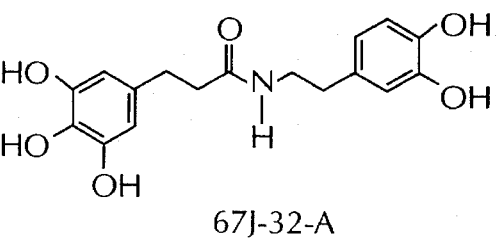
67J-32-A
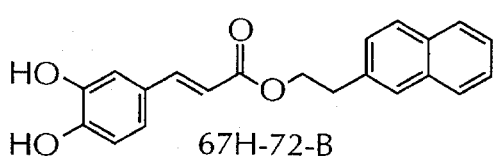
67H-72-B

METHOD FOR THE TREATMENT OF HYPERPROLIFERATIVE EPITHELIAL SKIN DISEASES BY TOPICAL APPLICATION OF HYDROXYLATED AROMATIC PROTEIN CROSS-LINKING COMPOUNDS

FIELD OF THE INVENTION

The present invention relates to a novel method of treating hyperproliferative epithelial diseases. In particular, a specific class of compounds is used in the topical treatment of skin lesions. These compounds are in general, hydroxylated aromatic protein crosslinking agents and are useful for a wide range of skin diseases.

BACKGROUND OF THE INVENTION

Non-neoplastic and neoplastic hyperproliferative skin disorders are prevalent and present an everincreasing burden to health care providers. Increased exposure of skin to UV light in recent years has contributed to the marked increased incidence of premalignant lesions such as actinic keratoses. Superficial squamous and basal cell carcinoma levels now exceed 700,000 cases per year in the US (American Cancer Society, 1994). Similarly warts (plantar and genital) and other localized hyperproliferative conditions of the skin are extremely prevalent.

At the present time, there are insufficient effective treatment options available to the clinician. Treatment modalities for these conditions include surgical resection or freezing the tissue to destroy rogue cells. These methods are not always the treatment of choice as they are non-selective and, hence, hyperproliferative cells can remain to cause recurrence or normal tissue can be damaged with the development of scar tissue. These techniques are often painful and therefore unacceptable to patients. Exfoliative acidic compounds such as salicylates are used topically to desquamate hyperproliferative skin lesions and kill cells directly, particularly in the treatment of plantar warts. However this treatment is not selective for hyperproliferative cells and is not always curative. The topical application of cytotoxic agents such as bleomycin and 5-fluorouracil (5FU) is used for the treatment of premalignant and malignant lesions and podophyllotoxin for genital warts. There is some concern about the toxicity of these agents, which work by direct cytotoxicity, interfering with DNA synthesis of proliferating cells by a variety of mechanisms. These agents have to be applied extremely carefully to avoid contact with normal skin since normal skin can be irreparably damaged, and systemic absorption of these compounds may also provide a significant risk to the patient. Retinoids, which are vitamin A derivatives, are a recent introduction for the treatment of neoplastic skin lesions. Unfortunately, these compounds are suppressive rather than curative and withdrawal of the drug leads to recurrence.

The epidermis forms the outermost layers of skin. This organ undergoes a process of continuous renewal in which the inner layer of epidermal cells, epidermal keratinocytes, continuously proliferate then undergo terminal differentiation leading to programmed cell death by the cross-linking of cellular proteins by transglutaminase enzymes to form cornified envelopes, which form the stratum corneum. This process is altered in hyperproliferative skin diseases, especially in virally induced warts, actinic keratoses and neoplasms but also in other hyperproliferative conditions (Yuspa S. H., Cancer Res., 54, 1178–1189, 1994, Molecular Biology of the Skin—the keratinocyte, eds Darmon and Blumenberg, Chapter 7, 207–243, 1993).

An object of the present invention is to provide a method of treating hyperproliferative epithelial diseases by the topical application of a class of compounds, which are hydroxylated aromatic protein cross-linking agents. Hyperproliferative epithelial diseases treatable by this method include most skin diseases wherein the growth control mechanisms have been disrupted. Examples of such diseases are papilloma virus infected cells commonly associated with warts and premalignant and malignant superficial neoplasias of the skin. In addition, cervical hyperproliferative conditions can be topically treated by the method of the present invention.

It is another object of the present invention to use cinnamic acid derivatives and analogs thereof including saturated forms thereof and especially methyl 2,5-dihydroxycinnamate in the treatment of hyperproliferative epithelial lesions. Methyl 2,5-dihydroxycinnamate is a preferred member of the class of compounds useful in the present invention and is highly efficacious as a topical formulation in the treatment of hyperproliferative epithelial lesions, particularly in the treatment of basal and squamous cell carcinomas.

It is yet another object of the present invention to use hydrophobic hydroxylated aromatic protein cross-linking compounds in treatment of skin diseases with more cornified lesions, such as plantar warts. These compounds exhibit good tissue penetration and therefore can be used to treat epithelial diseases below the stratum corneum.

SUMMARY OF THE INVENTION

The present invention relates to a method for the treatment of hyperproliferative epithelial diseases by topical application of hydroxylated aromatic protein cross-linking compounds. This class of compound comprises the compounds of the following general formulae:

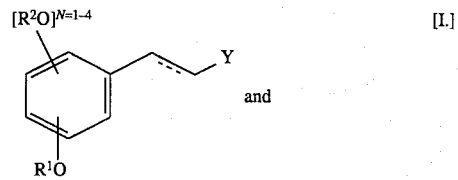

and

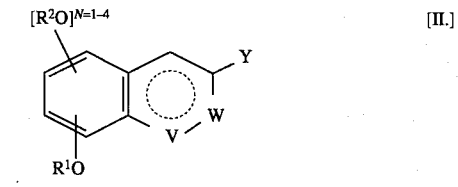

$R^1, R^2 = H$;

where Z=alkyl, aryl, aralkyl or alkaryl
Y=H, alkyl; aralkyl, alkaryl; aryl; hetaryl;

where Q=H, alkyl-O, N; O-alkaryl; O-aralkyl; N-alkaryl; or N-aralkyl.

- - - in Structure I, the dotted line represents an optional double bond and in Structure II, the dotted circle represents all degrees of saturation within the ring.

The above formulas are further defined in that the aralkyl and alkaryl groups are preferably $C_2$–$C_{13}$ in size, the aryl is preferably $C_6$–$C_{12}$, the hetaryl may contain a heteroatom such as, N, O and/or S. In formula II, each individual V and W can be carbon or a heteroatom such as N, O or S.

The present invention relates to the use of hydroxylated aromatic protein crosslinking compounds for the treatment of neoplastic and non-neoplastic hyperproliferative skin diseases. In particular, the present invention provides a topical treatment for a wide range of localized hyperproliferative epithelial disorders, including warts, cervical tumors, premalignant lesions such as actinic keratoses and benign and malignant tumors. One preferred embodiment uses methyl 2,5-dihydroxycinnamate (herein referred to as "MC") by topical application.

The present invention relates to hydroxylated aromatic protein crosslinking compounds for the inhibition in the growth of human tumor and HPV-infected cells. The present invention also induces changes in cell proteins similar to the changes which occur during normal skin formation, thereby changing hyperproliferative cells to a more normal type. Toxicity of the compounds of the present application has been tested utilizing mouse skin as a mode in vivo system. Because of the dual mechanisms of action, that is, growth inhibition and a protein cross-linking action, the agents of the present invention are a useful addition to the clinician armamentarium for these hyperproliferative skin disorders.

BRIEF DESCRIPTION OF THE FIGURES AND COLOR DRAWINGS

Color drawings are also described herein.

FIG. 1. MC Increases Cross-linked Protein in Epidermal Cell Lines. Black squares represent HPV 18 human epithelial keratinocytes; black circles represent SV 40 infected human keratinocytes; black triangles represent (SQCC-Y1) cells; white triangles represent (SP-1) benign tumor mouse keratinocytes; white squares represent (308 cells) benign mouse keratinocytes; and white circles represent (I-7) cells mouse squamous cell carcinoma.

Morphology of cross-linked protein envelope structures induced by MC SP-1 cells.

FIGS. 2A and 2B, 2C and 2D show color phase contrast photographs. SP-1 cells were treated with vehicle (A and C) or 250 µM MC (B and D) for 48 hours. In A and B phase contrast photomicrographs were taken. In C and D, cells were scraped into 2% SDS, 20 mM DTT and were boiled for 10 mins, then photographs were taken of the resultant samples to show the formation of cross-linked cornified envelopes.

FIGS. 3A and 3B. A: Time course for cornification of primary mouse keratinocytes in response to MC. Boxes represent 14 mM $Ca^{2+}$, triangles represent 100 µM MC, 1.4 mM $Ca^{2+}$, and solid circles represent 1 mM MC, 1.4 mM $Ca^{2+}$. B: MC Inhibits MTT Reduction Within 4 Hours in Primary mouse Keratinocytes. Cells were incubated in medium with 1.4 mM $Ca^{2+}$ and MC for 4 hours, then were incubated with MTT (0.5 mg/ml in medium) for a further 4 hours before determination of formazan production.

FIG. 4. Cross-linked Protein Production vs Growth Inhibition in Mouse Primary Keratinocytes. Cell growth is represented by black squares and cross-linked protein production by white squares. Results are ±SD (n=3) of one experiment, representative of three.

FIG. 5. Cross-linked Protein Production vs Growth Inhibition in A431 (human cervical cancer) Cells. Cell growth is represented by black circles and crosslinked protein production by white circles. Results are ±SD (n=3) of one experiment, representative of three.

FIG. 6. Transglutaminase Inhibitors do not Prevent Protein Cross-linking by MC. Hatched columns represent treatment with no transglutaminase inhibitor; black columns represent treatment with LTB 2 at 100 µM; and white columns represent treatment with HPB 2 at 100 µM. Results are from one experiment conducted in triplicate ±SD, which was replicated in two separate determinations.

FIG. 7. MC does not Increase Transglutaminase Activity in mouse Primary Keratinocytes. Black columns represent untreated cells in 1.4 mM $Ca^{2+}$ medium; and hatched columns represent cells treated with 1 mM MC. Cytosol is represented by "C" and membrane fractions are represented by "M". Results are ±SD (n=2) and were repeated in a similar experiment.

FIGS. 8A and 8B. MC Induces Cross-linked protein in Primary Mouse Keratinocytes at 4° and 37° C. "C" represents control samples. Results are of one experiment ±SD, conducted in duplicate, which was replicated in a separate experiment.

FIGS. 9A, 9B, 9C, 9D and 9E show color photographs. Topical Application of MC on Athymic Nude Mouse Skin. Histological sections were taken from paraffin-embedded tissue and were stained with hematoxylin and eosin. Panel a is vehicle control; panel b is 100 µM MC; panel c is 1 mM MC; panel d is 10 mM MC; and panel e is 100 mM MC. Magnification is 200x.

FIGS. 10A and 10B. MC inhibits Grafted SP-1 cell Tumor Formation. Numbers above bars denote the number of animals with tumors/the number of animals in the group. In panel A, MC was applied twice weekly for two weeks. In panel B, MC was applied on 5 days each week for three weeks.

FIG. 11. Cross-linked Protein Production in SQCC-Y1 Cells by MC Derivatives.

FIG. 12. Chemical Structure of hydroxylated aromatic protein crosslinking compounds described in Examples 9 and 10, results shown in FIG. 11.

FIGS. 13A, 13B and 13C show color photographs of mice. MC does not Cause Acute Inflammation or Necrosis when Applied Topically to Nude Mouse Skin. Photographs were taken after animal sacrifice upon termination of the experiments.

DETAILED DESCRIPTION OF THE INVENTION

Figure 1:
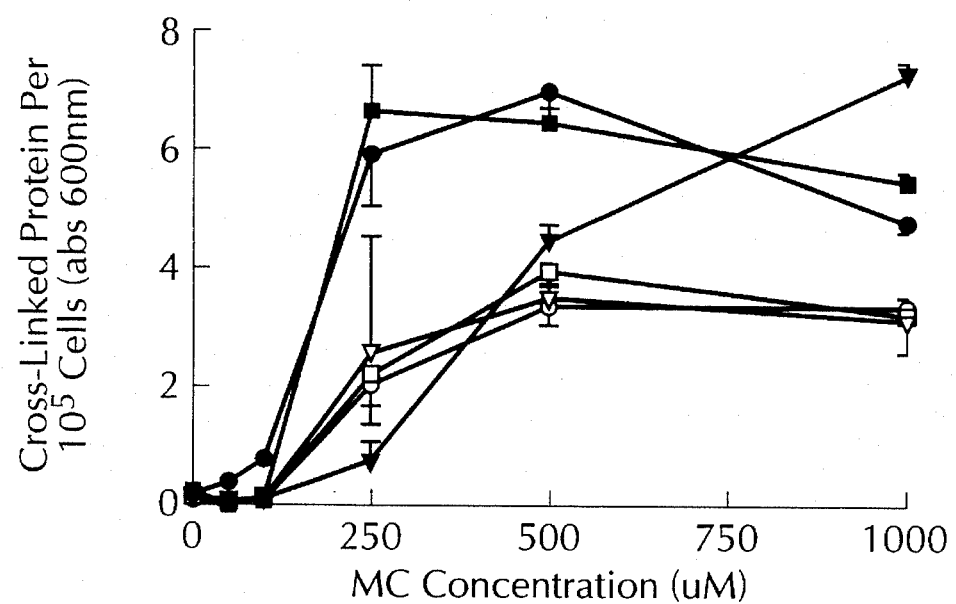

The hydroxylated aromatic protein crosslinking compounds of the present invention are a specific group of compounds with chemical protein cross-linking activity at high concentrations. This cross-linking effect described herein is novel and of unique significance for hyperproliferative disorders of the epithelium in which topical administration targets the drug to its specific site of action and cells are killed by a process which mimics epidermal cell differentiation.

The present invention provides hydroxylated aromatic compounds which serve as effective protein cross-linking agents and produce protein envelopes similar to those generated by the endogenous process of terminal differentiation in keratinocyte-derived cells. All cell types tested responded to the hydroxylated aromatic protein crosslinking compounds of the present invention by cross-linking, giving the agent potential for the topical treatment of a wide range of localized hyperproliferative epithelial disorders, including warts, premalignant lesions such as actinic keratoses and benign and malignant tumors The term "lesion" as used herein is defined as a circumscribed pathological tissue alteration, or a point or patch of a skin disease.

The cross-linking effect of the hydroxylated aromatic compounds of the present invention is rapid and leads to cell death for aberrant cell eradication. At lower concentrations, hydroxylated aromatic protein crosslinking compounds inhibit cell growth and tyrosine kinases (Umezawa et al. FEBS Lett., 314, 3, 289–292, 1992, Hori et al., J. Antibiot., 45, 280–282, 1992, Umezawa et al., FEBS Lett. 260, 198–200, 1990). These effects are also beneficial for the treatment of hyperproliferative disorders. The difference between concentrations required for these effects and cross-linking suggests that cross-linking is independent of the tyrosine kinase inhibitory properties of MC. Furthermore, other established tyrosine kinase inhibitors, including tyrphostins, herbimycin A and lavendustin A are unable to induce cross-linking (see Table II). At 4° C., cellular processes and enzymatic activity are inhibited. However hydroxylated aromatic protein crosslinking compounds, in particular MC, are able to induce cross-linked protein effectively at 4° or 37° C., showing clearly that chemical rather than biological processes are involved.

In vivo studies using MC reveal the lack of toxicity of MC to normal epidermis, suggesting that during topical application to the specific lesion, avoidance of normal skin may be less critical than with cytotoxic agents currently in use. This may be a reflection of the inability of MC to penetrate the stratum corneum. This effect may be beneficial in poorly differentiating hyperproliferative disorders, such as basal cell carcinoma, in which MC specifically targets cells of the diseased area.

In more cornified hyperproliferative disorders such as plantar warts, greater tissue penetration might be necessary, and more lipid soluble hydroxylated aromatic protein crosslinking compounds can be used. Examples of hydroxylated aromatic protein crosslinking compounds which are more lipid soluble are 67H-69A, 67H-98A, 67H-124A, 67G-146A. These compounds, due to their increased hydrophobicity, will penetrate the skin more readily and therefore be efficacious in the treatment of more cornified disorders of the skin, such as plantar warts. In addition, these compounds have enhanced stability.

The class of compounds useful in the method of the present invention is thought to act by a specific mechanism. It is known that ortho or para-hydroxylated aromatics can undergo facile oxidation to the corresponding quinones. The resulting quinones are then susceptible to attack by nucleophiles. Therefore, it appears that crosslinking of the hydroxylated aromatic compounds may occur by initial oxidation to reactive quinone intermediates which then undergo bis-addition of nucleophile (for example SH or $NH_2$ side chain groups of proteins), resulting in crosslinking.

One hydroxylated aromatic protein crosslinking compound of the present invention, MC, has a short half life in serum (Hori et al, J. Antibiot., 45, 280–282, 1992). This may be advantageous in that the compound can exert its local cross-linking effect rapidly (FIG. 3), then will be diluted and degraded in the bloodstream, rendering it inactive and preventing systemic side effects.

Particular emphasis is on compounds possessing ortho or para-substituents on the aromatic ring. The hydroxyls may be protected in prodrug form from degradation for enhanced penetration into cells. An example of such prodrug derivatization is esterification. Esterases would liberate the active, free hydroxy compounds once inside the cell. The form of the Y substituent in the general formulae would also be expected to have an effect on cellular penetration. For example, lipophilic ester groups would be expected to enhance crossing cell membranes.

The potency of hydroxylated aromatic protein crosslinking compounds to induce protein cross-linking is cell type-specific, suggesting that the compound may exert some specificity for certain hyperproliferative conditions. The increased sensitivity of mouse primary keratinocytes for the cross-linking effect is not related to the normal phenotype. For example, primary cultures of normal human epidermal keratinocytes from foreskin did not respond to MC with respect to its cross-linking effects at less than 250 uM MC. Studies using a grafting model demonstrated the ability of MC to inhibit tumor formation at 1 and 100 mM concentrations. Hydroxylated aromatic protein crosslinking compounds induce the cross-linking of cell proteins into cornified envelope-like structures, causing cell death by a non-biological mechanism which emulates the normal differentiation program of epidermal keratinocytes. In addition to their growth inhibitory properties, the unique protein cross-linking ability of the class of compounds described in the instant invention proffers a new mechanism for the topical treatment of hyperproliferative diseases of the skin.

One embodiment of the present invention uses an erbstatin analog, methyl 2,5-dihydroxycinnamate, which forms cross-linked protein envelopes in normal and neoplastic epithelial cells by a mechanism independent of tyrosine kinase inhibition. Methyl 2,5-dihydroxycinnamate (MC) is a tyrosine kinase inhibitor. To assess its ability to induce epithelial cell differentiation, crosslinked protein envelopes were measured after a 48 h incubation with agent. In all cells tested (primary keratinocytes, mouse SP-1, 308 (papilloma), 1–7 (carcinoma) cells and human lines SQCC-Y1 (squamous carcinoma), A431 (epidermoid carcinoma) and HPV18 or SV40-infected keratinocytes), MC increased cross-linked protein in a dose-dependent manner (0.1–1 mM). To confirm differentiation, MC-treated mouse primary keratinocytes were tested for transglutaminase (TGase) activity, inhibition of protein cross-linking by the TGase inhibitor LTB-2 and HPB-2 and incorporation of the fluorescent TGase substrate dansylcadaverine into envelopes. Results refuted the involvement of TGase in the mode of action of this agent. MC also induced protein envelopes in NIH 3T3 fibroblasts, even when incubated at 4° C. in phosphate buffered saline, suggesting a non-physiological process. Simultaneous application of dithiothreitol (DTT, 20 mM) to 3T3 cells prevented cross-linking by MC at 37° and 4° C. Western blot analysis of an in vitro assay with EGF receptor showed that DTT did not prevent tyrosine kinase inhibition by MC, but did inhibit MC-induced mobility retardation of the EGF receptor, suggesting that oxidation of agent or an acceptor group is permissive for cross-linking. The present invention demonstrates that MC does not induce differentiation in epithelial cells, but causes chemical protein cross-linking at high dose. This effect, in concert with growth inhibitory properties, may be useful clinically in the topical treatment of warts or superficial neoplasias of the skin.

In a further method of use, the invention comprises a method of preventing the growth of benign, premalignant and malignant cells by prophylactically applying said composition comprising hydroxylated aromatic protein crosslinking compounds, such as MC to a particular body site which may be abnormally exposed to a cancer inducing stimulus.

The present invention has also been found to be effective not only in eliminating or ameliorating tumors, but in preventing their occurrence when applied prophylactically. To prevent the establishment of cancer, hydroxylated aromatic protein cross-linking agents of the present invention can be formulated into creams and ointments or in cosmetic bases to be used daily, preferably topically.

The efficacious amount of hydroxylated aromatic protein crosslinking compound used in the method of the instant invention may be varied over a wide range. The typical range of the amount of a hydroxylated aromatic protein crosslinking compound in the instant methods is between about 0.0001 wt % and 5 wt % and preferably, the amount of hydroxylated aromatic compounds applied according to the present invention ranges between about 0.001 wt. % and 2 wt. %. As used herein, the weight percent in the formulations refers to the concentrations of materials being effectively delivered to the treatment site.

Generally, the efficacious amount and concentration of the compound to be applied are those which result in the composition exhibiting the property or properties required in the treatment for which the composition is being used, namely, anti-tumor activity. In particular, the compounds of the present invention cause protein cross-linking and cell death. This phenomenon is advantageous in the treatment of hyperproliferative epithelial lesions in that it promotes normal cell characteristics. The preferred amounts depend upon the particular condition being treated, the rate of delivery of the active ingredients to the treatment site, and the number of applications of the formulation which can be used. Preferred amounts for any specific application may be determined by normal pharmacological screening methods used in the art. If desired, an excess of the compound can be used as appropriate for the specific condition being treated. It has been found that it is necessary to contact the tumor cells with at least a threshold amount of the compounds of the present invention to observe an inhibition in growth of the skin neoplasm. This minimum amount has been found to be greater than about 10 nanomoles of the compound per milliliter of tumor cells.

Carrier materials are well known in the pharmaceutical formulation art and include those materials referred to as diluents or vehicles. The carrier may include inorganic or organic materials and should have sufficient viscosity to allow spreading of the composition and provide good adherence to the tissue to which it is topically applied. Examples of such carriers include, without limitation, polyols such as glycerol, propylene glycol, polyethylene glycol, preferably of a molecular weight between about 400 and about 8000, suitable mixtures thereof, vegetable oils, and other materials well known to those skilled in the art. The viscosity of the formulation can be adjusted by methods well known in the art, for example, by the use of a higher molecular weight polyethylene glycol.

In addition to the hydroxylated aromatic protein crosslinking compound and carrier, the formulation can contain pharmacologically-acceptable additives or adjuvants such as antimicrobial agents, e.g. methyl, ethyl, propyl, and butyl esters of para-hydroxybenzoic acid as well as chlorobutanol, phenol, ascorbic acid, etc. The formulation can also contain thickening or gelling agents, emulsifiers, wetting agents, coloring agents, buffers, stabilizer and preservatives including antioxidants such asbutylhydroxyanisole in accordance with the practice of the art. The formulation can also contain penetration enhancers such as dimethyl sulfoxide, long-chain alcohols such as nonoxynol, long-chain carboxylic acids, propylene glycol, N-(2-hydroxyethyl)pyrrolidone, 1-dodecyl-azacycloheptan-2-one, and the like. Depending on the method of application and the disease being treated, it may be desirable to use absorption-delaying agents such as aluminum monostearate and gelatin.

The composition of the formulation can be adjusted using components well-known in the formulation art to provide a pharmaceutical formulation which is a gel, cream, ointment, solid, liquid, semi-solid, etc. The particular physical form of the formulation depends on the desired method of treatment and the patient to be treated.

Typical formulations of the pharmaceutical compositions of this invention are set forth in Table I. In the embodiments described, the preferred concentration range is 1 mg/100 ml–2 g/100 ml, or 0.0001%–5% w/w. For derivatives which are unstable in an aqueous environment, the following formulations for topical application are provided. A preferred ointment can be prepared by mixing the hydroxylated aromatic compound in 1 ml 100% ethanol, then mixing into white petrolatum or lanolin. A simple formulation for a lotion may be prepared by simply mixing the hydroxylated aromatic compound of the present invention in 100% ethanol. Alternatively, a hydrophilic petrolatum can be prepared by mixing all of the ingredients except for the cholesterol (see Table I) together and heating until melted. Once melted, the cholesterol is added. This mixture is stirred until all of the components are dissolved. When cold, triturate hydroxylated aromatic compound previously dissolved in 1 ml of 100% ethanol. For derivatives which are stable in an aqueous environment, additionally the following formulation is preferred: Water (up to 20%) can be added to the hydrophilic petrolatum described above to produce a water in oil emulsion.

For cold creams, melt all ingredients (see Table I) except sodium borate and water at 70° C. The sodium borate is dissolved in water and then added to the non-aqueous ingredients, stirring until cold.

The concentrations of active ingredients in a particular formulation required to provide a particular effective dose may be determined by a person skilled in the pharmaceutical formulation art based upon the properties of a carrier and the particular additives introduced into the formulation. It is contemplated that formulations can be prepared that have significantly higher concentrations of the compound of the present invention depending upon the carrier and additives being used. If the carrier substantially retains the compound or releases it at a slow rate, the concentrations of the compound in the formulation can be substantially increased and in fact may have to be substantially increased in order to provide an effective treatment. In practice, it is preferred that a formulation contain the lowest concentrations of active ingredient which effectively treat the condition with the desired number of applications, i.e., a lower effective dose rate can be tolerated if multiple applications are used. This low concentration limit is dependent upon the delivery effectiveness of the carrier vehicle. Preferably, the compounds of the present invention comprises between about 0.0001 and about 5 weight percent of the formulation.

TABLE I

| Application Form | Formulation | Grams |
|---|---|---|
| Ointment | Hydroxylated Aromatic Compound (Stable in aqueous environment) | (about 0.0001 – 5% w/w) |
| | Peg 400 | 4.2 |
| | Peg 8000 | 61.7 |
| | Water | 19.0 |
| | Ascorbic acid | 0.1 |
| Gel | Hydroxylated aromatic compound stable in aqueous environment | (about 0.0001 – 5% w/w) |
| | Standard denatured alcohol | 12.0 |
| | Propylene glycol | 22.5 |
| | Water | 53.4 |
| | Non-ionic surfactant | 6.0 |
| | Xantham gum | 4.0 |
| | Ascorbic acid | 0.1 |
| Cream | Hydroxylated aromatic compounds (Stable in aqueous environment | (about 0.0001 – 5% w/w) |
| | Ascorbic acid | 0.1 |
| | Benzyl alcohol | 5.0 |
| | Propylene glycol | 23.0 |
| | Water | 35.4 |
| | Stearyl alcohol | 7.0 |
| | Cetyl alcohol | 4.5 |
| | White petrolatum | 13.0 |
| | Poloxyl-40 stearate | 7.0 |
| Solid | Hydroxylated aromatic compound (Stable in aqueous environment) | (about 0.0001 – 5% w/w) |
| | Carnuba wax | 8.9 |
| | Beeswax | 13.3 |
| | Lanolin anhdrous | 4.4 |
| | Cetyl alcohol | 4.4 |
| | Ascorbic acid | 0.1 |
| | Castor oil | 57.7 |
| | Water | 1.2 |
| Ointment | Hydroxylated aromatic compound | (about 0.0001 – 5% w/w) |
| | White petrolatum or lanolin | 100 g |
| | Ethanol 100% | 1 ml |
| Hydrophilic ointment | Hydroxylated aromatic compound | (about 0.0001 – 5% w/w) |
| | Cholesterol | 30 g |
| | Stearyl alcohol | 30 g |
| | White wax | 80 g |
| | White petrolatum | 860 g |
| Cold cream | Hydroxylated aromatic compound | (about 0.0001 – 5% w/w) |
| | Cetyl esters wax | 125 |
| | White wax | 120 |
| | Mineral oil | 560 |
| | Sodium botate | 5 |
| | Purified water | 190 ml |

A preferred embodiment of the instant invention comprises compositions containing MC, i.e., methyl dihydroxycinnamate. This composition has been found to be particularly effective in treating tumorous skin lesions in animal studies. Although the effective concentration of MC delivered to the treatment site depends, inter alia, upon the carrier and other additives included in the formulation, ordinarily the concentration of MC in the formulation will range from about 0.0001 to about 5 weight percent. These ranges are provided by way of description and not by way of limitation since it is recognized that the concentration may be adjusted over a wide range depending on the carrier material, number of applications used, etc., as described hereinabove.

In topical applications, the instant compositions are applied to the affected area or afflicted situs of the patient. The term "topical" refers herein to the surface of the epidermal tissue, especially the skin, the surface of tumors on the skin which have been debrided or otherwise modified, as well as sites from which solid tumors have been removed from the skin. Alternatively, topical can refer to application of a formulation to a cervical lesion.

In preparing a formulation suitable for topical application, the instant compositions are normally mixed with a suitable solvent. Examples of solvents which are effective for this purpose include ethanol, acetone, acetic acid, aqueous alkaline solutions, dimethyl sulfoxide, glycerin, glycerol, propylene glycol, nonoxynol, ethyl ether, polyethylene glycol, etc.

In addition, antioxidants such as ascorbic acid (preferably at 0.1%), hydroxyquinone, sodium bisulfite, meta bisulfite, etc. can be added to the formulation.

The following examples used particular methods in carrying out the experiments illustrative of the present invention. These experiments represent non-limiting examples of the present invention. Other embodiments would be readily apparent to the skilled artisan and are considered within the scope of the present invention.

EXAMPLE 1

Reagents.

Figure 10A:
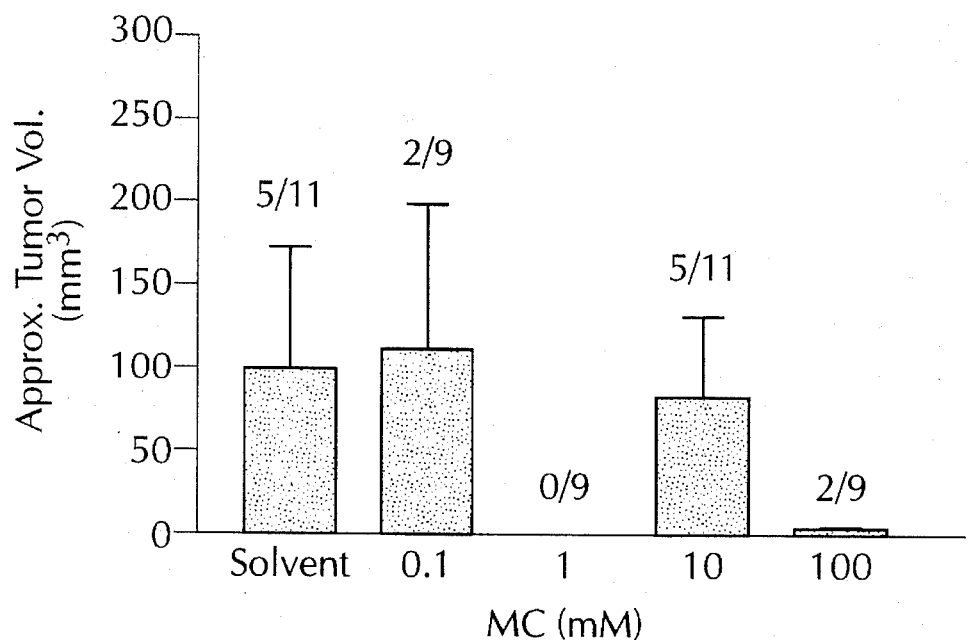
Figure 10B:
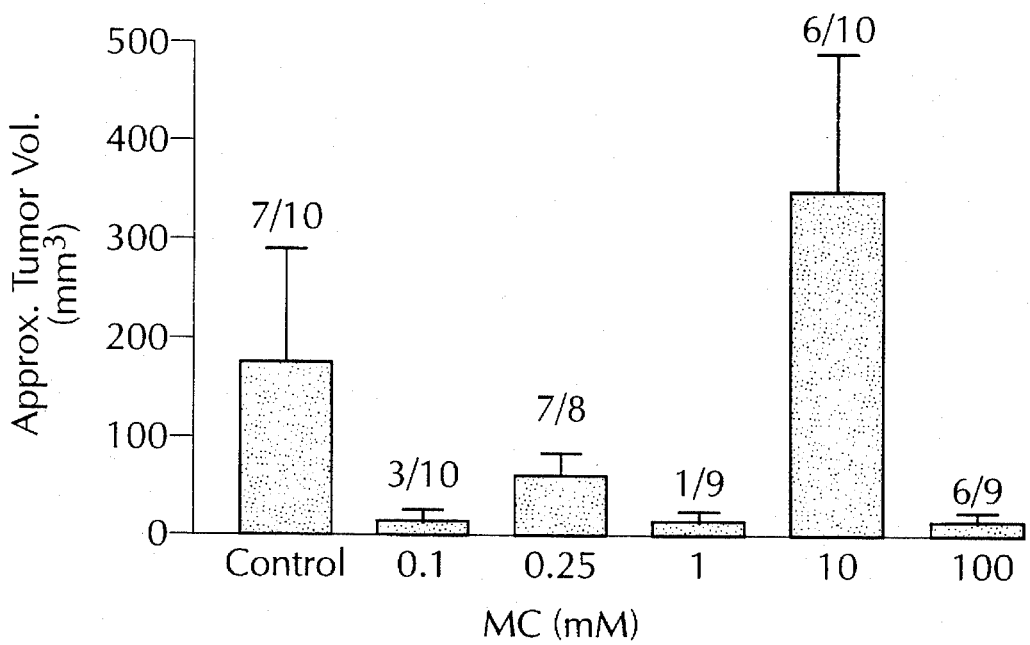

Methyl 2,5-dihydroxycinnamate (MC) and the tyrosine kinase inhibitors listed in table II were obtained from LC Laboratories, Woburn, Mass, Compounds related to MC (FIG. 10) were synthesized within the laboratory of Dr. T. R. Burke, NCI, Bethesda. 3-(4,5-dimethylthiazol-2-yl)-2,5-diphenyl tetrazolium bromide (MTT) was obtained from Sigma.

Cell Culture.

Primary mouse keratinocytes were isolated from BALB/c newborn mouse skin. Primary keratinocytes, the benign neoplastic keratinocyte cell lines 308 and SP-1 (Strickland et al, Cancer Res., 48, 165–169, 1988) and the mouse squamous cell carcinoma line 1–7 (Greenhalgh et al., Proc. Natl. Acad. Sci., 87, 643–647, 1990) were grown in Eagle's minimal essential medium with 8% fetal calf serum (FCS) (chelexed) and penicillin 20 iu/ml, streptomycin 20 ug/ml (P/S). Unless otherwise indicated, the $Ca^{2+}$ concentration in medium was adjusted to 0.05 mM (Hennings et al., Cells, 19, 245–254, 1980). A431 human epidermoid carcinoma cells were obtained from ATCC, Rockville, Md., and were routinely passaged in DMEM with 10% FCS, P/S, glutamine (2 mM) and pyruvate (1 mM). SQCC-Y1 human squamous carcinoma cells and non-tumorigenic HPV 18 and SV 40 infected human keratinocytes were kindly donated by Dr. James Rheinwald of Harvard University, Boston, Mass. and Dr. Richard Schlegel of Georgetown University, Washington D.C. respectively. Human cells were cultured in DMEM/Ham's F12 1:1, 10% FCS, P/S and epidermal growth factor 10 ng/ml.

MC Increases Cross-linked Protein in Epidermal Cell Lines.

Cells were incubated with MC for 48 hours, then cross-linked protein was isolated and measured as described in Example 1. Results are of one experiment ±SD (n=3) and are representative of 2–3 separate determinations, as shown in FIG. 1. MC induced crosslinked envelope production in human and mouse keratinocyte-derived cell lines which represent the normal phenotype (mouse primary keratinocytes), hyperproliferative (SV 40 infected), wart-like (HPV 18 infected), actinic keratosis-like (SP-1, 308), and carcinoma cells (A431, SQCC-Y1, 1-7) (FIGS. 1–5).

EXAMPLE 2

Time Course for Cornification of Primary Mouse Keratinocytes in Response to MC.

Primary mouse keratinocytes were incubated with MC for 0, 0.5, 1, 4 and 48 hours and were processed as follows.

Cornified Envelope Assay.

The assay measures insoluble cross-linked protein envelopes as described (Hough-Monroe et al. Analytical biochem., 199, 25–28, 1991), with modifications as follows. Cornified envelopes were prepared by scraping monolayers into 2% sodium dodecylsulphate (SDS), 20 mM dithiothreitol (DTT) in phosphate buffered saline (PBS). Unattached cells were pelleted from medium and were resuspended in SDS/DTT and pooled with attached cells. Samples were boiled for 10 mins. Cornified envelope samples were examined under the microscope using phase contrast optics or were applied to an RC60 membrane (Schleicher and Schuell, Keene, N.H.) on a 96-well dot-blot apparatus attached to a vacuum. Samples were washed three times with SDS/DTT and the resultant protein spots on RC60 membrane were fixed and stained as described. Sports were excised and eluted with 1% $NH_3OH$ concentrated solution, 66% methanol (200 ul) overnight. Absorbance of eluate was measured on a Titertek plate reader at 600 nm.

Figure 3A:
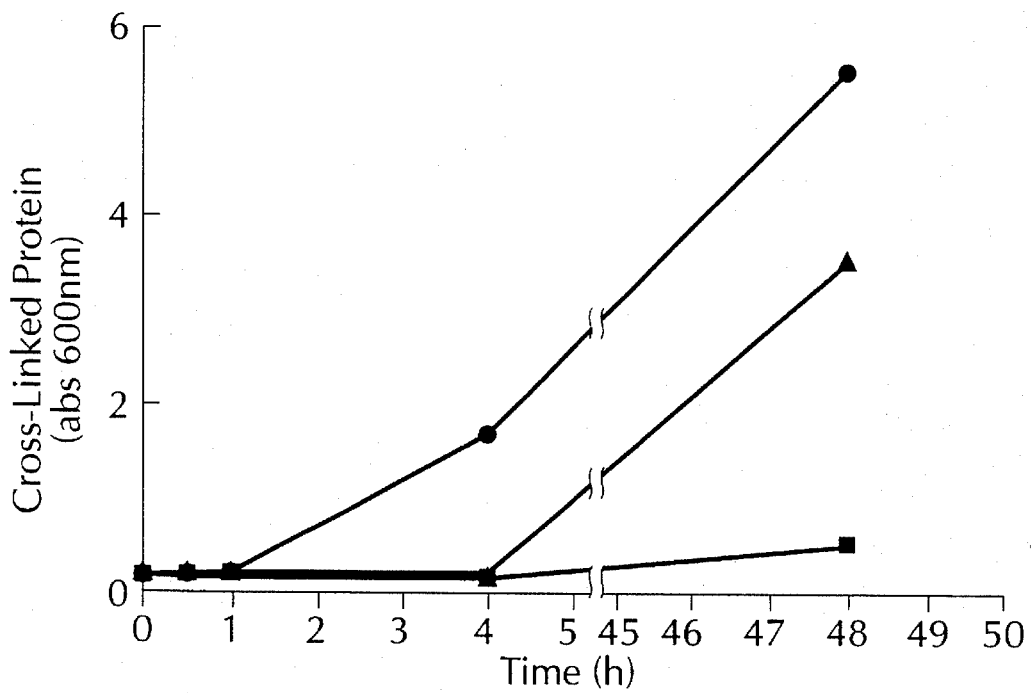
Figure 2A:
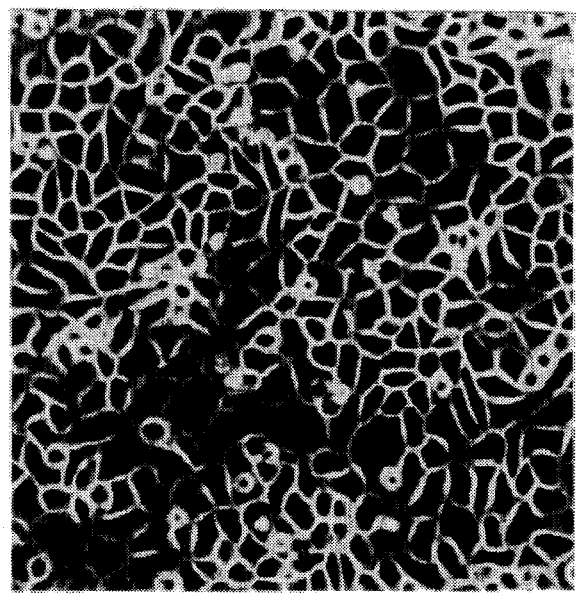
Figure 2B:
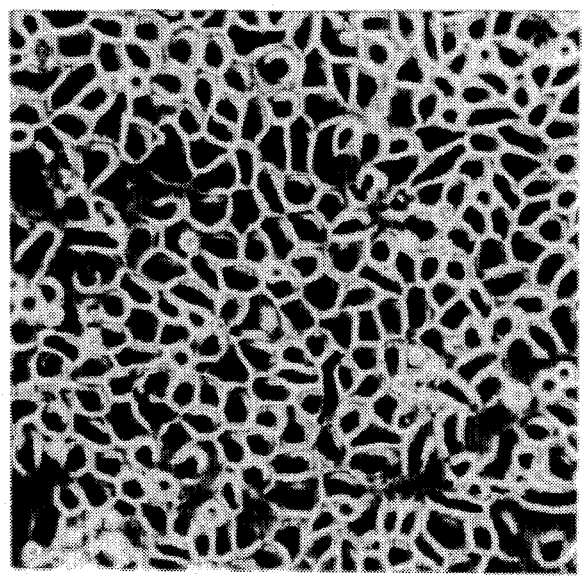
Figure 2C:
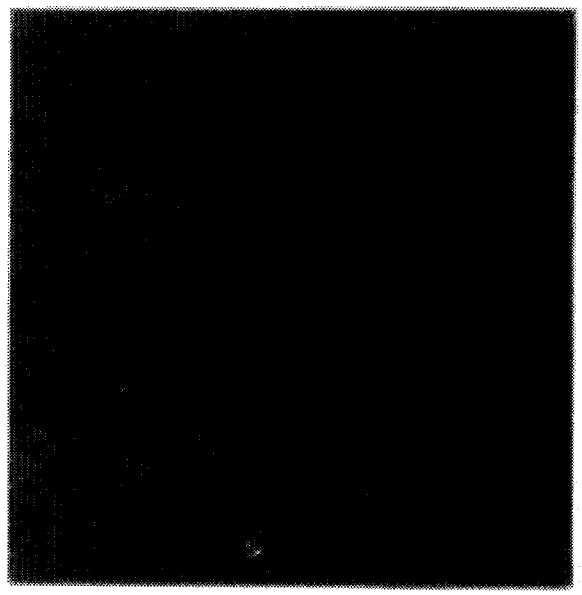
Figure 2D:
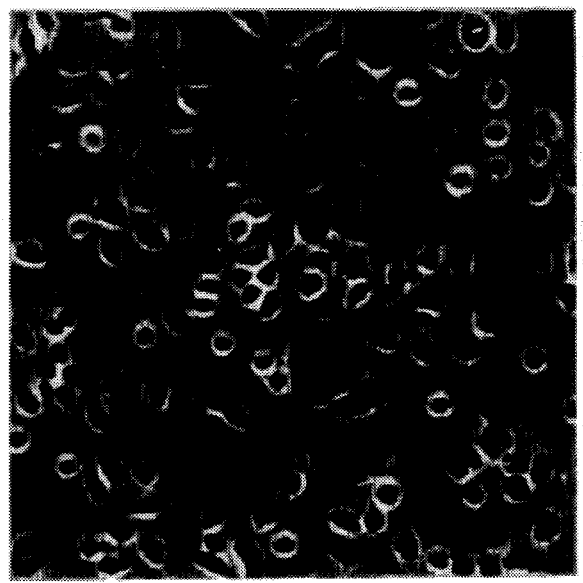

Cornification occurred at 1 mM within 4 hours of treatment of the cells. After 48 hours both the 1 mM and 100 µM dosages were effective in cornifying the primary keratinocytes (FIG. 3A).

MTT Cytotoxicity Assay.

MTT is a dye which is reduced by mitochondrial dehydrogenase enzymes to a blue formazan product. Ability of cells to reduce MTT can be used to measure cell viability (Mosmann T., J. Immunol. Methods, 65, 55–63, 1983). Cells were incubated in 96 well plates with or without MC for the indicated time, then were incubated for a further 4 hours with 0.5 mg/ml MTT. Medium was removed and 88.9% DMSO, 11.11% glycine buffer (100 mM glycine, 100 mM NaCL pH 10.5) was added to each well. Plates were shaken for 20 minutes to allow formazan dissolution, then absorbance was measured on a plate reader at 570 nm.

EXAMPLE 3

Cross-linked Protein Production vs Growth Inhibition in Mouse Primary Keratinocytes.

Figure 3B:
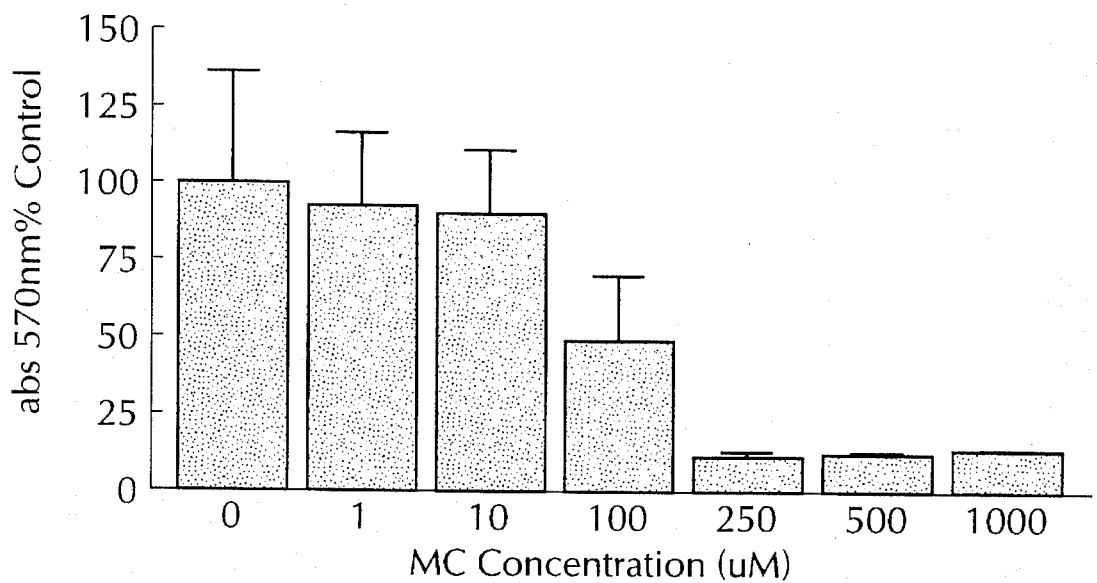

Cells were seeded at low density and were treated with MC for 3 days. Cells were then counted and increase in cell number was compared to untreated controls, or cells were processed for cross-linked protein. (FIG. 4) Protein cross-linking was rapid, commencing within 4 hours at 1 mM in mouse primary keratinocytes, (FIG. 3A) and was accompanied by cell death, as measured by the MTT assay (FIG. 3B).

Cross-linked Protein Production vs Growth Inhibition in A431 Human Epidermoid Carcinoma Cells.

Figure 5:
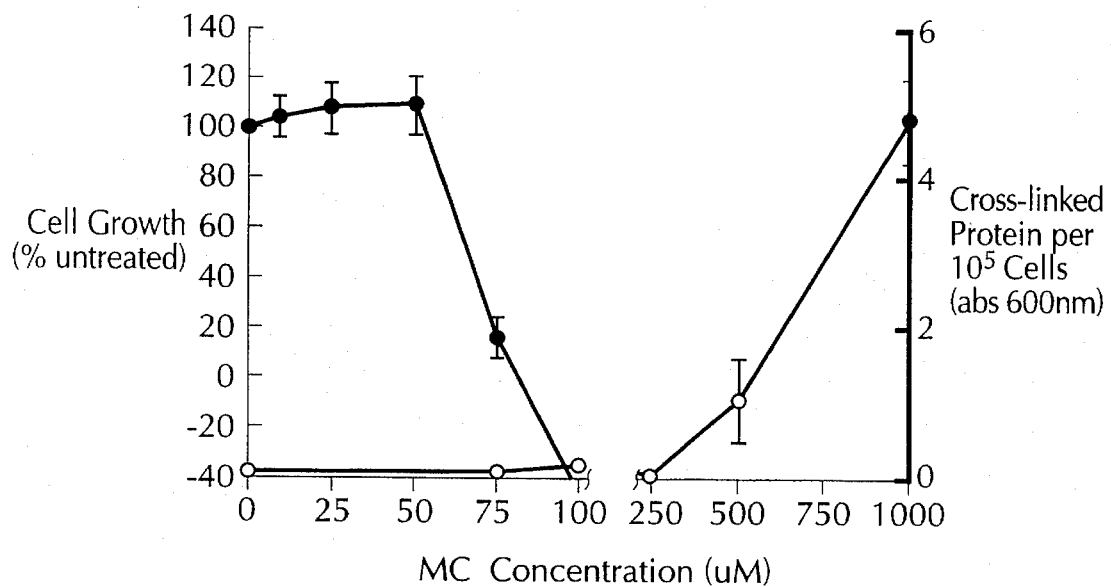

Cells were seeded at low density and were treated with MC for 3 days. Cells were then counted and increase in cell number was compared to untreated controls, or cells were processed for cross-linked protein (FIG. 5).

Figure 4:
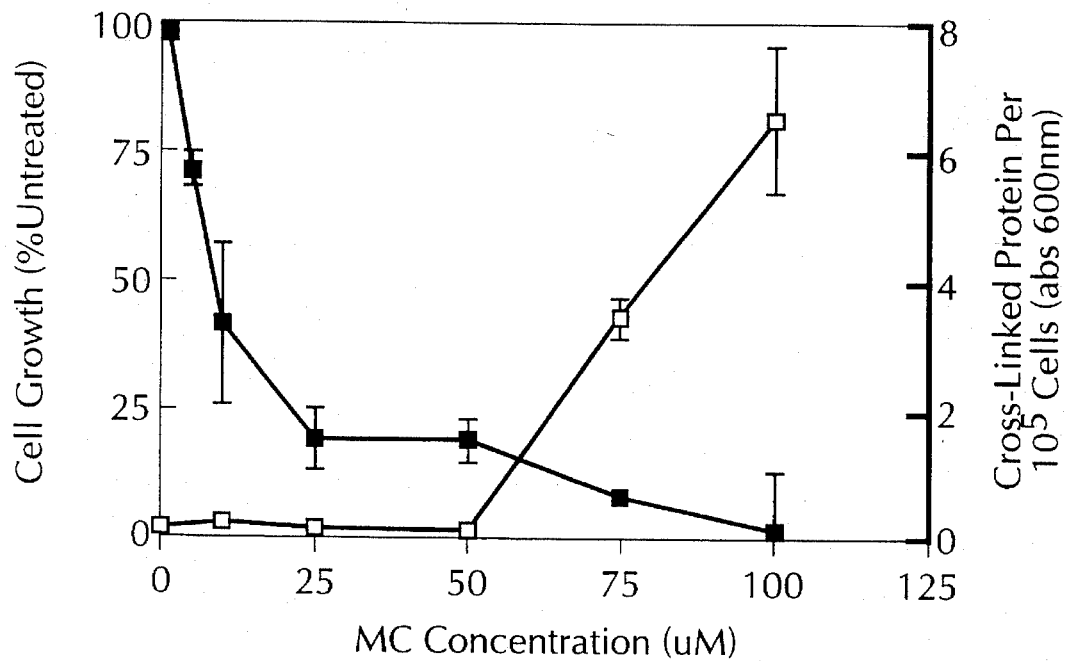

These results suggest that the concentration of MC required to effect cell growth is lower than that required to facilitate protein cross-linking. For example, in primary mouse keratinocytes, only 20% of the cells continued to grow at 25 µM MC, while more than 50 µM MC was required to produce protein cross-linking. In A431 cells, 75 µM MC inhibited cell growth significantly, whereas the protein cross-linking affect was not evident at concentrations less than 250 µM. Therefore it is clear that the cross-linking of proteins occurs at higher concentrations than those required to inhibit cell growth (FIGS. 4 and 5).

EXAMPLE 4

Transglutaminase Inhibitors do not Prevent Protein Cross-linking by MC.

Figure 6:
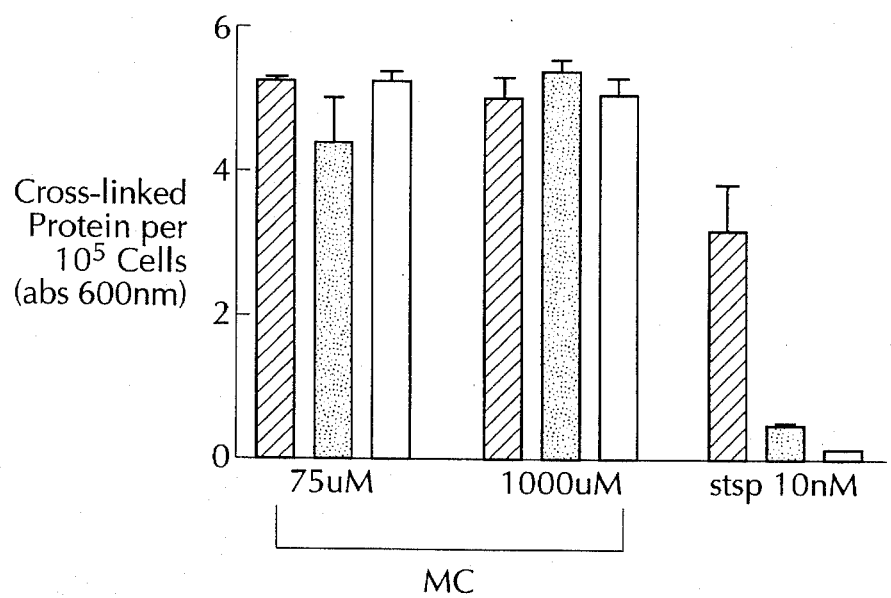
Figure 8A:
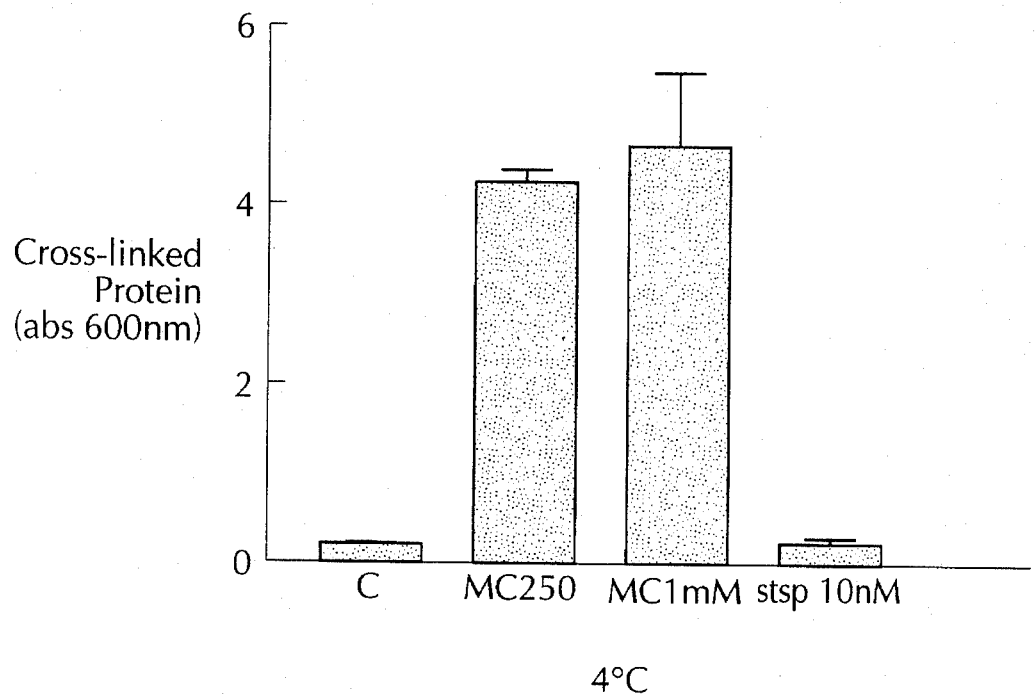
Figure 8B:
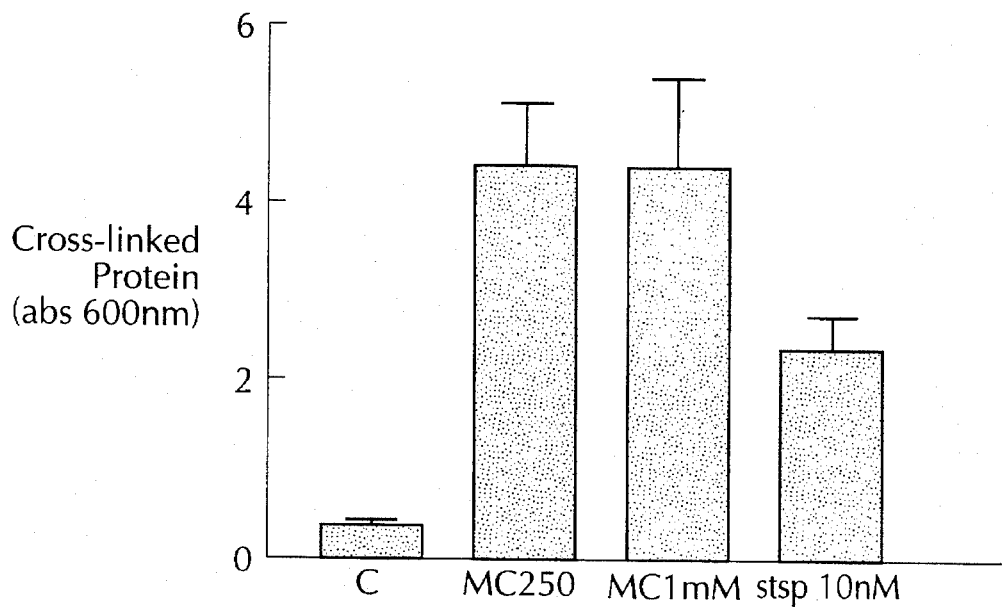
Figure 9A:
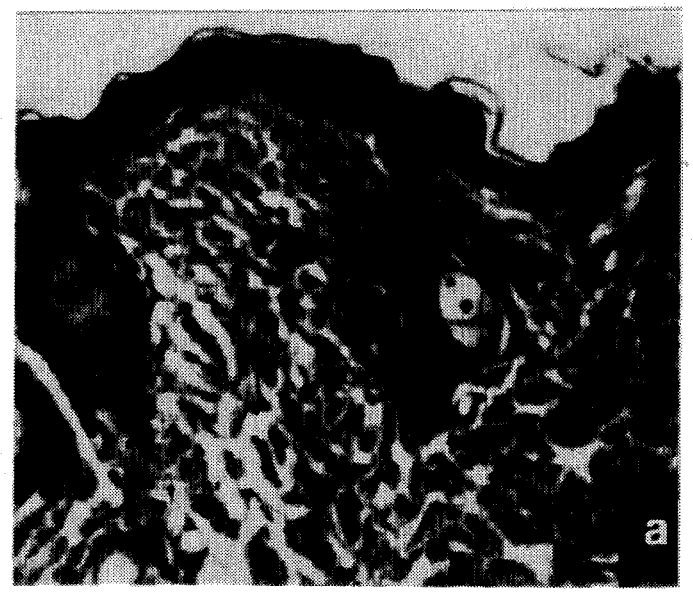
Figure 9B:
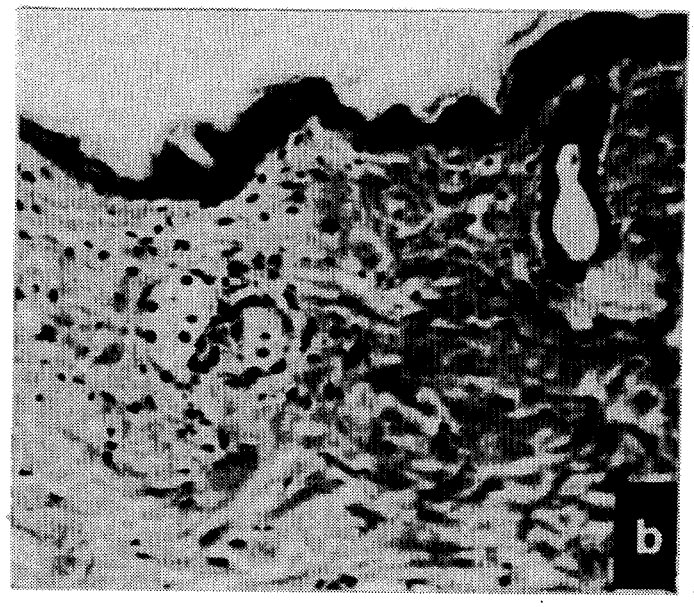
Figure 9C:
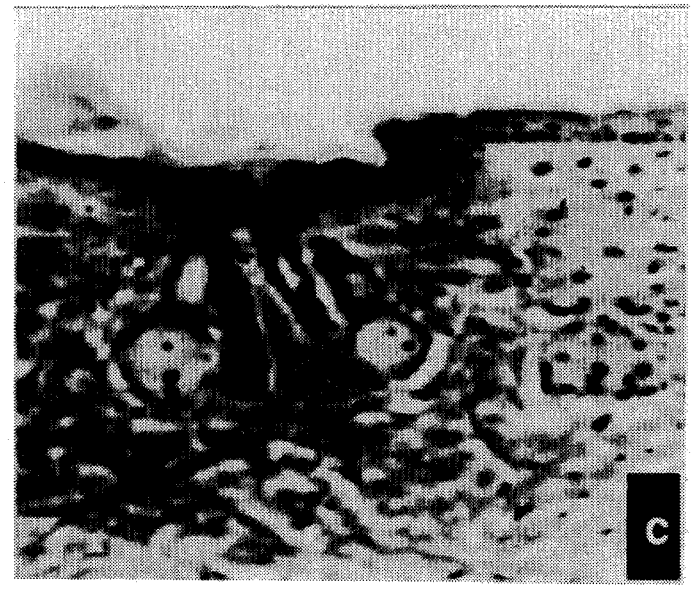
Figure 9D:
Figure 9E:

Primary mouse keratinocytes were incubated with either 75 µM or 1000 µM MC or staurosporine (stsp) at 10 nM for 48 hours, with or without the transglutaminase (TGase) inhibitors LTB 2 and HPB 2, both used at 100 µM. Inhibitors were added 30 mins before MC or stsp (FIG. 6). Cross-linked protein was measured by the cornified envelope assay, described in Example 2. The results shown in FIG. 6 demonstrate that MC cross-linking activity is not affected by transglutaminase inhibitors, as is the activity of staurosporine.

MC does not Increase Transglutaminase Activity in Mouse Primary Keratinocytes.

Mouse primary keratinocytes were incubated in medium with 1.4 mM $Ca^{2+}$ for the indicated times. MC-induced cross-linking commences within 4 hours (see FIG. 3). Cells were separated into cytosol (C) and Triton-X100 soluble membrane (M) fractions (FIG. 7). Each fraction was standardized for protein and was assayed for transglutaminase activity using the method of Lichti et al., J. Biol. Chem., 260, 1422–1426 (1985). The results of the experiment demonstrate that transglutaminase is not stimulated by treatment of cells with MC during the time period in which its cross-linking activity is seen (4 hrs) as compared to untreated cells. Protein cross-linking was not inhibited by transglutaminase (TGase) inhibitors unlike that induced by the kinase inhibitor staurosporine, which increases TGase activity (Dlugosz and Yuspa, Cancer Res., 51, 4677–4684, 1991) (FIG. 6), and cellular TGase activity did not increase at the commencement of cross-linking by MC (FIG. 7), suggesting that the endogenous cross-linking enzymes were not involved in this effect.

EXAMPLE 5

MC Induces Cross-linked Protein in Primary Mouse Keratinocytes at 4° C. and 37° C.

Cells were incubated in medium with MC or staurosporine (stsp) at 4° C. or 37° C. for 48 hours, then cross-linked protein was isolated and measured by the cornified envelope assay as described in Example 2. Cross-linking by MC took place at 4° C. and 37° C., suggesting a non-biological process (but rather, a chemical process) unlike that by staurosporine, which was temperature dependent.

EXAMPLE 6

A range of tyrosine kinase inhibitors was tested for ability to produce cross-linked protein envelopes in 308 and SQCC-Y1 cells. All inhibitors were obtained commercially from LC Laboratories, Woburn, Mass. Concentrations used were within the range for inhibition of tyrosine kinases. Concentration of tyrphostins was limited by solubility in medium at 37° C.

TABLE II

| TYROSINE KINASE INHIBITOR | CONCENTRATION RANGE TESTED | CROSS-LINKED PROTEIN |
| --- | --- | --- |
| lavendustin A | 10 nM–10 uM | — |
| compound 5 | 10 nM–20 uM | — |
| herbimycin A | 10 nM–20 uM | — |
| psi-tectorigenin | 10 nM–20 uM | — |
| tyrphostin A23 | 0.1–500 um | — |
| tyrphostin A47 | 0.1–500 uM | — |
| tryphostin B42 | 0.1–500 uM | — |
| tyrphostin B66 | 0.1–250 um | — |
| bis tyrphostin | 0.1–200 uM | — |

Table II. Tyrosine Kinase Inhibitors do not Induce Protein Cross-linking.

None of the tyrosine kinase inhibitors exhibited the protein cross-linking activity seen with the hydroxylated aromatic protein crosslinking compounds of the present invention. This finding indicates that the hydroxylated aromatic compounds of the present invention do not operate as by virtue of their tyrosine kinase inhibitor activity. In fact, there appears to be no correlation between the two activities.

EXAMPLE 7

Topical Application of MC on Athymic Nude Mouse Skin.

Figure 13A:
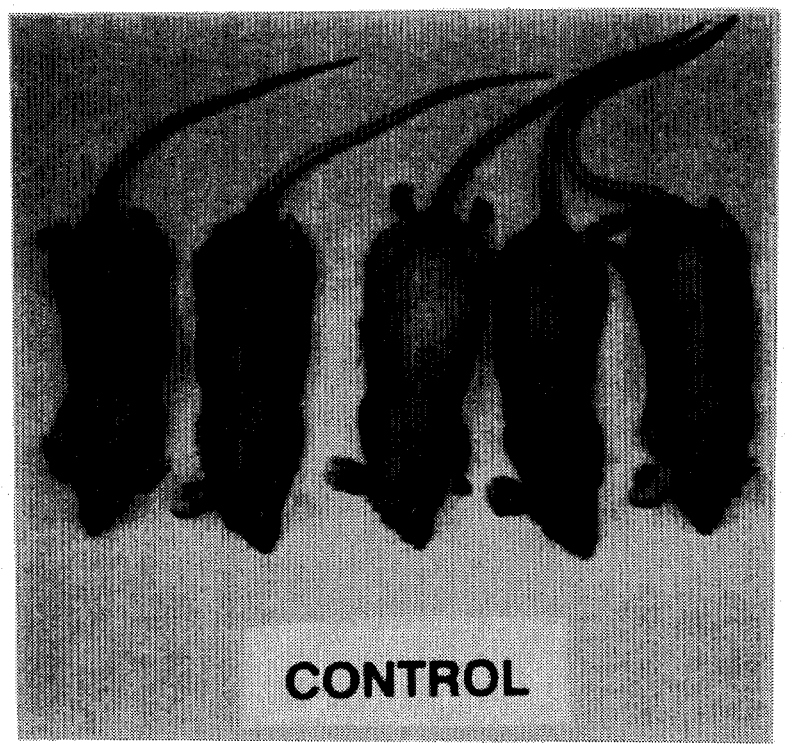
Figure 13B:
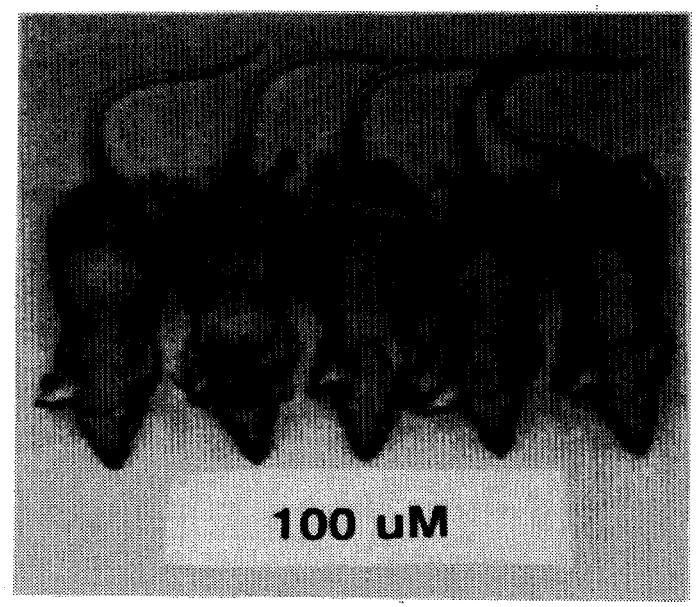
Figure 13C:
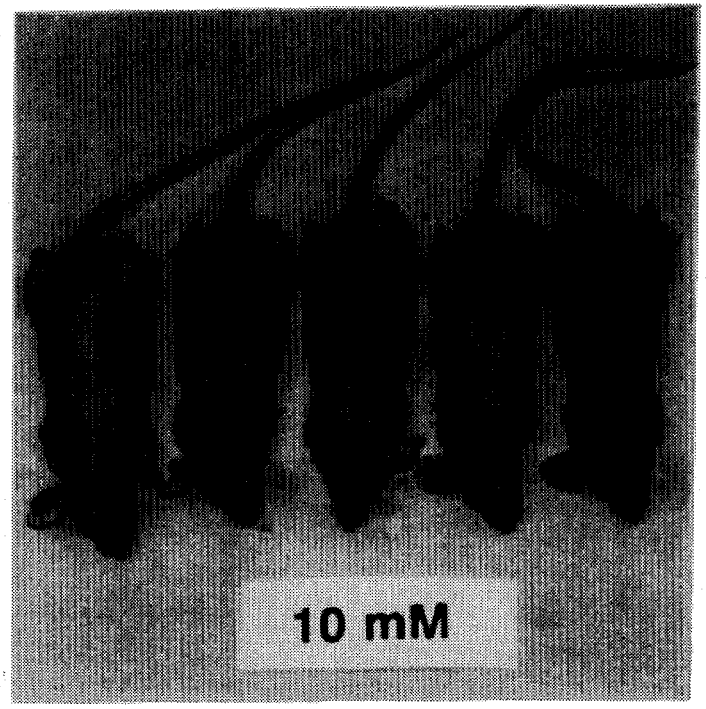

Acute topical toxicity of MC was assessed by its application to athymic mouse skin and observation for inflammation, ulceration or other signs of toxicity after 5x weekly applications for 2 weeks and by microscopical analysis of paraffin-embedded sections of athymic mouse skin after MC application. Male nu/nu mice, 8 weeks old, were subdivided into 5 treatments groups and MC was administered topically in 10% DMSO in acetone vehicle. Mice were treated with a control vehicle, 100 µM MC, 1 mM MC, 10 mM MC or 100 mM MC. Treatment was 5 times per week for two weeks, after which animals were sacrificed and dorsal skin was fixed in Carnoy's solution at 4° C. for 24 hours followed by ethanol 100%. Histological sections were taken from paraffin-embedded tissue and were stained with hematoxylin and eosin. FIG. 13 illustrates the effect of MC on the skin of nude mice.

MC does not Cause Acute Inflammation or Necrosis when Applied Topically to Nude Mouse Skin.

Male nu/nu mice, 8 weeks old, were subdivided into treatment groups and MC was administered topically to dorsal skin in 10% DMSO in acetone vehicle (25 µl). Treatment was 5 times per week for two weeks. Throughout a two week period of topical treatment with MC to nude mouse dorsal skin, animals were observed for signs of systemic toxicity or changes in skin at the application site. No changes were observed (FIG. 13), except for patchy brown discoloration at 100 mM. MC itself is yellow-brown, so some discoloration would be expected due to drug deposition and accumulation at this high concentration. Using microscopy, MC was not acutely toxic or inflammatory to normal athymic mouse skin up to 10 mM. The highest concentration tested, 100 mM, caused some vacuolation of epidermal cells and focal inflammatory infiltrates were visible, but with no obvious necrosis (FIG. 9).

EXAMPLE 8

Skin Grafting and In vivo Treatments.

Skin grafting was performed on athymic nude mice using $0.5 \times 10^6$ SP-1 cells with $8 \times 10^6$ newborn SENCAR mouse dermal fibroblasts as described (Strickland et al., *Carcinogenesis*, 14, 205, 1993). Domes (plastic covers placed over the site of skin grafting) were removed one week after grafting, and after a further week, topical application of MC commenced. The agent was applied in 25 ul 90% acetone, 10% DMSO vehicle. Weekly, tumor measurements were recorded up to 5 weeks after grafting.

MC Inhibits Grafted SP-1 Cell Tumor Formation.

Grafting was performed as described above. In one group of mice, MC was applied twice weekly for two weeks (shown in FIG. 10A). In a second group of mice, MC was applied on 5 days each week for three weeks (shown in FIG. 10B). Tumors were measured using calipers at the termination of the experiment and tumors were fixed and sections were taken to confirm the tumor phenotype by microscopy. MC inhibited the growth of tumors derived from the neoplastic cell line SP-1 grafted onto the backs of nude mice at 1 mM and 100 mM concentrations.

EXAMPLE 9

Synthesis of several hydroxylated aromatic protein crosslinking reagents.

Petroleum ether was of the boiling range 35°–60° C. and removal of solvents was performed by rotary evaporation under reduced pressure. Silica gel filtration was carried out using TLC grade silica gel (5–25µ Aldrich). Melting points were determined on a Mel Temp II melting point apparatus and are uncorrected. Elemental analyses were obtained from Atlantic Microlab Inc., Norcross, Ga., and are within 0.4% of theoretical values unless otherwise indicated. Fast atom bombardment mass spectra (FABMS) were acquired with a VG Analytical 7070E mass spectrometer under the control of a VG 2035 data system. $^1$H NMR data were obtained on Bruker AC250 (250 MH$_z$) instrument.

Synthesis of Cinnamic Acid Analogues.

The synthesis of cinnamic acid analogues was achieved by straight forward application of literature techniques. Two general approaches, designated "method A" and "method B" were utilized:

Method A: Synthesis of Caffeic acid β-phenylethyl ester (CAPE, 67H-42-A).

A solution of 1.80 g (10.0 mmol) of caffeic acid, 17.9 mL (150 mmol) of β-phenylethyl alcohol and 100 mg of p-toluenesulfonic acid in benzene (100 mL) were stirred overnight at reflux with a Dean Stark trap. Solvent and excess alcohol were removed by distillation and residue purified by silica gel chromatography (petroleum ether/CHCl$_3$). Product was crystallized (ether/petroleum ether) to provide 67H-42-A as snow-white crystals, 1.0 g (35%): mp 128.0° C. 126°–128° C.) (Grunberger, D. et al., *Experimentia*, (1988) 44:230–2).

3,4-Difluorocinnamic acid β-phenylethyl ester (67J-17-A).

Reaction of 3,4-difluorocinnamic acid and β-phenylethyl alcohol as outlined in method A provided 67J-17-A as snow-white crystals (38% yield): mp 53°–57° C., $^1$H NMR (CDCl$_3$) δ:7,49 (d, 1H, J=16 Hz), 7.30–7.05 (m, 8H) 6.27 (d, 1H, J=16 Hz), 4.36 (t, 2H, J=7.0 Hz), 3.82 (s, 3H), 2.95 (t, 2H, J=7.0 Hz); FABMS (NBA, +VE m/z 289 (M+H). Anal. ($C_{17}H_{14}O_2F_2$) C,H.

Method B: Synthesis of 2.5-dihydroxycinnamic acid β-phenylethyl ester (67H-124-A).

A mixture of 2,5-dihydrobenzaldehyde (138 mg. 1.0 mmol), 430 mg (0.93 mmol) of (carboxymethyl)-triphenylphosphonium chloride, β-phenylethyl ester [mp 162°–165° C. (dec); 148°–151° C.] (Bankova, V., et al., *J. Nat. Prod.* (1990) 53:821–4) and powdered anhydrous $K_2CO_3$ (586 mg, 4.24 mmol) in anhydrous DMF (2 mL) were stirred at ambient temperature overnight. The crude reaction mixture was then partitioned between 0.5N HCl in brine (50 mL)/ethyl acetate (3×50 mL), washed with 05N HCl in brine (50 mL), brine (2×50 mL), dried ($MgSO_4$) and solvent removed to yield a dark syrup (577 mg). The crude product was passed down a silica pad using first $CHCl_3$ then 5% ethyl acetate in CHCl3. The resulting light yellow crystals were recrystallized from ether: petroleum ether to provide pure 67H-124-A as beige crystals (115 mg; 43% yield); mp 123°–125° C.; $^1H$ NMR ($CDCl_3$) δ:7.86 (d, 1H, J=16 Hz), 7.30–7-17 (m, 5H), 6.88 (d, 1H, J - 2.7 Hz), 6.70 (dd, 1H, J=2.7 Hz & 8.6 Hz), 6.64 (d, 1H, J=8.6 Hz), 6.44 (d, 1H, J=16 Hz), 4.36 (t, 2H, J=7.1 Hz), 2.96 (t, 2H, J=7.1 Hz); ABMS (NBA, −VE) m/z 283 (M—H). Anal. ($C_{17}H_{16}O_4$) C,H.

2,3,4-Trihydroxycinnamic acid β-phenylethyl ester (67H-80-C).

Reaction of 2,3,4-trihydroxybenzldehyde with (carboxymethyl)-triphenylphosphonium chloride, β-phenylethyl ester as described above in method B provided crude product which was purified by multiple passes down a silica pad with final crystallization from ether: petroleum ether, providing pure 67H-80-C as beige crystals in 19% yield: mp 144° C. soften, 147°–150° C.; $^1H$ NMR (DMSO-$d_6$) δ: 9.77 (s, 1H), 8.60 (s,1H), 7.78 (d, 1H, J=16 Hz), 7.36–7.18 (m, 5H), 6.95 (d, 1H, J=8.5 Hz), 6.37 (d, 1H, J=16 Hz), 6.36 (d, 1H, J=8.5 Hz), 4.31 (t, 2H, J=6.9 Hz), 2.95 (t, 2H, J=6.9 Hz); FABMS (NBA, −VE) m/z 299 (M—H). Anal. ($C_{17}H_{16}O_5$.1/4$H_2O$)C,H.

2,4,5-Trihydroxycinnamic acid β-phenylethyl ester (67H-98-A).

Reaction of 3,4,5-trihydroxybenzldehyde with (carboxymethyl) -triphenylphosphonium chloride, β-phenylethyl ester as described above in method B except that the reaction was run at ambient temperature for 2 h. Purification by multiple silica gel chromatographies yielded a light yellow foam. Trituration with petroleum ether: ether provided 67H-98-A as a light yellow solid in 21% yield: mp 146°–149° C.; $^1H$ NMR 9.62 (s, 1H), 9.52 (s, 1H0, 8.45 (s, 1H), 7.75 (d, 1H, J - 16 Hz), 7.37–7.18 (m, 5H), 6.87 (s, 1H), 6.38 (s, 1H), 6.16 (d, 1H, J=16 Hz), 4.30 (t, 2H, J=6.8 Hz), 2.95 (t, 2H, J=6.8 Hz); FABMS (NBA, −VE) m/z 299 (M—H). Anal. ($C_{17}H_{16}O_5$.1/4$H_2O$) C,H.

Caffeic acid 2-(2-naphthyl) ethyl ester (67H-72-B).

Reaction of caffeic acid and 2-(2-naphthyl)ethanol as outlined in method A except that the reaction time was increased to 3 days, provided product as a white solid following chromatography. Trituration with ether gave pure 67H-72-B as a snow-white solid in 3% overall yield: mp 174.5°–176.5° C.; $^1H$ NMR (DMSO-$d_6$) δ:9.61 (brs, 1H), 9.14 (brs, 1H), 7.93–7.78 (m, 5H), 7.52–7.42 (m, 3H), 7.04 (s, 1H), 6.99 (d, 1H, J=8.1 Hz), 6.76 (d, 1H, J=8.1 Hz), 6.24 (d, 1H, J=15.9 Hz), 4.43 (t, 2H, J=6.7 Hz), 3.14 (t, 2H, J=6.7 Hz); FABMS (NBA, −VE) m/z 333 (M—H). Anal. ($C_{21}H_{18}O_4$.1/$H_2O$) C, H.

Caffeic acid 2-(1 naphthyl)ethyl ester (67H-148-A).

Reaction of caffeic acid and 2-(1-naphthyl)ethanol as outlined in method A except that the reaction time was increased to 6 days, provided product 67H-148-A as a snow-white solid in 21% overall yield: mp 165°–168° C.; $^1H$ NMR (DMSO-$d_6$) δ:8.21 (d, 1H, J=8.1 Hz), 7.97–7.94 (m, 1H), 7.84 (t, 1H, J=5 Hz), 7.64–7.39 (m, 5H), 7.03 (d, 1H, J=1.8 Hz), 6.99 (dd, 1H, J=1.8 Hz & 8.1 Hz), 6.23 (d, 1H, J=15.9 Hz), 4.44 (t, 2H, J=7.0 Hz), 3.45 (t, 2H, J=7.0 Hz); FABMS (NBA, −VE) m/z 333 (M—H). Anal. ($C_{21}H_{18}O_4$.1/4$H_2O$) C, H.

3-(3,4-Dihydroxyphenyl ) propanoic aid β-phenylethyl ester (67H-69-A).

A solution of 2 (284 mg, 1.0 mmol) in ethanol (25 mL) was hydrogenated over 10% PdC (100 mg) under 40 psi $H_2$ in a Parr apparatus (2.5 h). The reaction mixture was filtered through celite and crystallized from ether: petroleum ether to provide product 67H-69-A as off-white crystals (175 mg, 61% yield): mp 72.5°–73.5° C., $^1H$ NMR (DMSO-$d_6$) δ:8.75 (s, 1H), 8.67 (s, 1H), 7.36–7.18 (m, 5H), 6.61 (d, 1H, J=8.0 Hz), 6.57 (d, 1H, J=1.9 Hz), 6.40 (dd, 1H, J=1.9 Hz & 8.0 Hz), 4.21 (t, 2H, J=6.9 Hz), 2.86 (t, 2H, J=6.8 Hz), 2.64 (t, 2H, J=6.9 Hz), 2.49 (t, 2H, J=6.8 Hz); FABMS (NBA, −VE)m/z 285 (M—H). Anal. ($C_{21}H_{18}O_4$)C,H.

6,7-Dihydroxy-2-naphthoic acid β-phenylethyl ester (67H-46-A).

A total of 346 mg (1.5 mmol) of 6,7-dimethoxy-2-naphthoyl amide (Burke, T. R., et al., *J. Med. Chem.* (1993) 36, 425–432) in 6N HCll (20 mL) was stirred at reflux (24 h) then cooled and 6,7-dihydroxy-2-naphthoic acid collected as a purple colored solid (260 mg). A 225 mg (1.10 mmol) portion was esterified with phenylethyl alcohol as described in method A (reaction time 2 days). Chromatographic purification ($CHCl_3$ followed by ethyl acetate) yielded a solid, which was suspended in $CHCL_3$ and collected by filtration to yield 67H-46-A as snow-white needles (100 mg, 25% yield overall): mp175°–176° C.; $^1H$ NMR (DMSP-$d_6$) δ8.33 (s, 1H), 8.24 (s, 1H), 7.66 (s, 2H), 7.38–7.17 (m, 6H), 4.50 (t, 2H, J=6.8 Hz), 3.07 (t, 2H, J=6.8 Hz); FABMS (NBA,−VE)mz 307 (M—H), Anal. ($C_{19}H_{16}O_4$.1/4$H_2O$) C,H.

5,6-Dihydroxy-2-naphthoic acid β-phenylethyl ester (67H-52-A).

A total of 240 mg (1.0 mmol) of 5,6-dimethoxy-2-naphthoic acid (Burke, T. R., et al., *J. Med. Chem.* (1993) 36, 425–432) was heated neat with pyridine.HCL (5.0 g) at 180°–200° C. under argon (40 minutes). Excess pyridine-.HCL was distilled off under high vacuum and residue mixed with 1N HCL (20 mL), giving 5,6-dihydroxy-2-naphtohoic acid a light yellow solid which was collected by filtration (160 mg). A 140 mg (0.7 mmol) portion was reacted β-phenylethyl alcohol as described for compound 67H-46-A and purified by silica gel chromatography ($CHC_3$) to provide product 67H-52-A as a white solid (1200 mg, 36% yield overall): mp 164°–166° C.; $^1HNMR$ (DMSO-$d_6$) δ8.40 (d, 1H, J=1.6 Hz), 8.07 (d, 1H, J=8.8 Hz), 7.80 (dd, 1H, J=1.6 Hz & 8.8 Hz), 7.49 (d, 1H, J=8.6 Hz), 7.38–7.33 (m, 5H), 7.25 (d, 1H, J=8.6 Hz), 4.51 (t, 2H, J=6.8 Hz), 3.08 (t, 2H, J=6.8 Hz); FABMS (NBA,−VE)mz 307 (M—H). Anal. ($C_{19}H_{16}O_4$) C,H.

5,6-Dihydroxy-2-naphthoic acid methyl ester (67G-146-A).

This compounds was prepared as previously described. (Burke, T. R., et al., *J. Med. Chem.* (1993) 36, 425–432).

6,7-Dihydroxyisoquinoline-3-carboxylic acid methyl ester hydrochloride (67F-65-A).

This compound was prepared as previously described. (Burke, T. R., et al., *Heterocycles* (1992) 34, 757–764).

7,8-Dihydroxyisoquinoline-3-carboxylic acid methyl ester hydrochloride (67F-36-A).

This compound was prepared as previously described. (Burke, T. R. et al., *Bioorg. Med. Chem. Lett.* (1992) 2, 1771–1774).

2-(3,4-Dihydroxyphenyl)-1-phenylacetamidoethane (67J-28-A). To a vigorously stirred mixture of tyramine.HCl (948 mg, 5.0 mmol) in aqueous $NaHCO_3$ (1.68 g, 20 mmol in 25 mL $H^2O$) and $CHCl_3$ (25 mL) was added phenylacetyl chloride (660 μL, 5.0 mmol) dropwise, then the reaction was stirred at ambient temperature (1 h). The organic layer was collected, combined with a 25 mL ($CHCl_3$ extract of the aqueous layer and the combined organic phases were washed with 1N HCl (25 mL), dried (MgSO$_4$) and solvent evaporated. The resulting foam was mixed with ethylacetate, then diluted with ether and a white solid (225 mg) removed and discarded. The filtrate was purified by silica gel chromatography using first 25% ethyl acetate in CHCl$_3$, then 100% ethyl acetate. Product 67J-28-A was obtained as a light yellow syrup (362 mg, 27% yield); $^1$H NMR (DMSO-d$_6$) δ: 7.38–7.24 (m, 5H), 6.37 (d, 1H, J=8.0 Hz), 6.62 (d, 1H, J=2 Hz), 6.40 (dd, 1H, J=2 Hz & 8.0 Hz), 5.63 (brt, 1H), 3.14 (dt, 2H, J=6.5 Hz & 13.0 Hz), 2.59 (t, 2H, J=6.5 Hz); high resolution FABMS calcd for C$_{16}$H$_{16}$NO$_3$ (M—H); 270.1130, Found 270.1117, Anal. (C$_{16}$H$_{17}$O$_3$) H,N; C theor. 69.69, found. 70.11.

3-(3,4-Dihydroxyphenyl) propanoic acid β-(3,4-dihydroxyphenyl)ethyl amido (67J-32-A).

To a solution of 348 mg (1.0 mmol) of 3-(3,4-dihydroxyphenyl) propanoic acid pentafluorophenyl ester, prepared as described in the previous reaction, in andydrous dimethylformamide (2 mL) was added tyramine.HCL 227 mg. 1.2 mmol) and triethylamine (209μ, 1.5 mmol) and the reaction stirred. After 2 h solvent was removed by distillation under high vacuum and residue purified by silica gel chromatography as described int he previous reaction to yield product 67J-32-A as a white foam (338 mg, quantitative yeld): $^1$H NMR (DMSO-d$_6$) δ: 8.75 (s, 1H), 8.72 (s, 1H), 7.84 (t, 1h<J=5.6 Hz), 6.65–6.57 (m, 4H), 6.44–6.39 (m, 2H), 3.20–3.11 (m, 2H), 2.52–2.46 (m, 2H), 2.28–2.22 (m, 2H); high resolution FABMS calcd for C$_{17}$H$_{18}$NO$_5$ (M—H): 316.1185, found 316.1146. Anal. (C$_{17}$H$_{19}$O$_5$1/2H$_2$O) H, N; C theor. 62.14, found 62.57.

EXAMPLE 10

Based on the initial observations that MC induces crosslinking, a series of 15 aromatic compounds were examined for similar activity. These compounds all possessed either ortho or para-hydroxyl substitution patterns except for 67-J17A, in which OH-groups were replaced with fluorine. Preliminary studies indicated that some compounds were able to cross-link, while others were weak or inactive at the concentrations tested. Four of the most potent compounds are shown in FIG. 12 as "67H-69A", "67H-98A", "67H-124A" and "67G-146A". These structures clearly exhibit protein cross-linking activity and are therefore members of the hydroxylated aromatic protein crosslinking compounds of the present invention. These particular hydroxylated aromatic protein crosslinking compounds are useful as topical agents in the treatment of hyperproliferative skin diseases.

Figure 11:
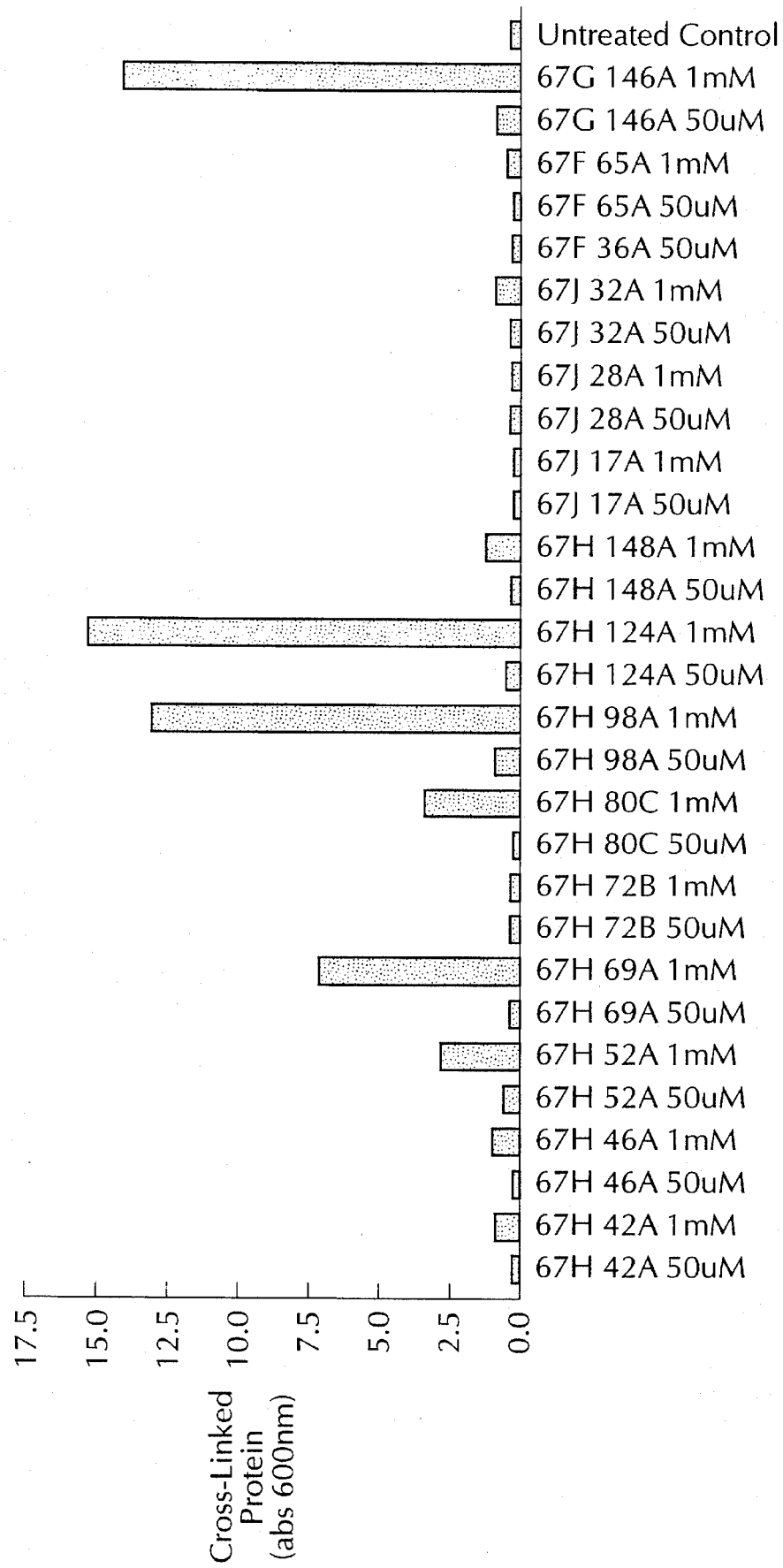

The results shown in FIG. 11 indicate that some structural specificity is involved in the crosslinking process. For example, active compound 67H-69-A differs from inactive 67H-42-A only by the absence of a side chain double bond. Furthermore, addition of a single hydroxyl to inactive 67H-42-A provides the active compound 67H-98-A. Another example of structural specificity is illustrated by comparison of active 67G-146-A with inactive 67F-36-A which differs by the inclusion of a ring nitrogen.

All of the references mentioned in the present application are incorporated in toto into this application by reference thereto.

We claim:

1. A method of treating hyperproliferative epithelial cell lesion comprising topically applying to the lesion an effective amount of a composition containing at least one compound of the formula:

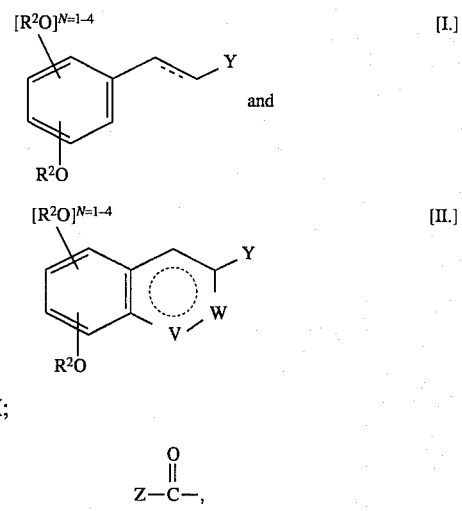

$R^1$, $R^2$=H;

where Z=alkyl, aryl, aralkyl or alkaryl;
Y=H, alkyl; aralkyl, alkaryl; aryl;

$$-\overset{O}{\underset{\|}{C}}-Q,$$

where Q=H, alkyl-O, N; O-alkaryl; O-aralkyl; N-alkaryl; or N-aralkyl;

- - - represents an optional double bond and V and W=nitrogen or carbon, wherein the alkyl, aralkyl, alkaryl are 2 to 13 carbons in size, and the aryl is 6 to 12 carbons in size.

2. The method according to claim 1 wherein the epithelial lesion is a skin lesion.

3. The method according to claim 1 wherein the epithelial lesion is a human papilloma virus-infected tissue lesion.

4. The method according to claim 1 wherein the epithelial lesion is a tumorous lesion.

5. The method according to claim 1 wherein the compound is methyl 2,5-dihydroxycinnamate.

6. The method according to claim 1 wherein the compound is

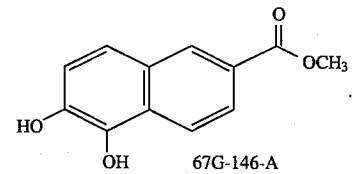

7. The method according to claim 1 wherein the compound is

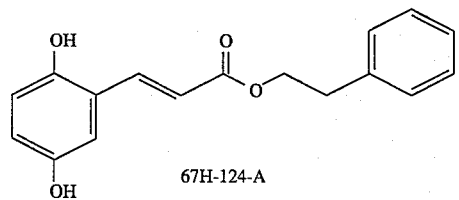

8. The method according to claim 1 wherein the compound is

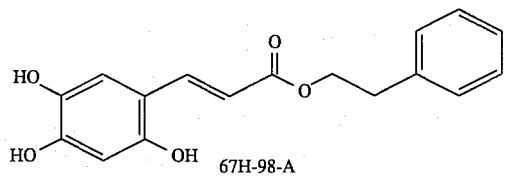
67H-98-A
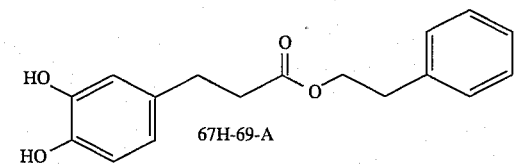
67H-69-A
9. The method according to claim 1 wherein the compound is
* * * * *